United States Patent [19]

Husain

[11] Patent Number: 5,304,698

[45] Date of Patent: Apr. 19, 1994

[54] SOLID CATALYZED SUPERCRITICAL ISOPARAFFIN-OLEFIN ALKYLATION PROCESS

[75] Inventor: Altaf Husain, Marlton, N.J.

[73] Assignee: Mobil Oil Corporation, Fairfax, Va.

[21] Appl. No.: 927,753

[22] Filed: Aug. 10, 1992

[51] Int. Cl.$^5$ .............................................. C07C 2/58
[52] U.S. Cl. ..................................................... 585/722
[58] Field of Search ......................................... 585/722

[56] References Cited

U.S. PATENT DOCUMENTS

| | | | |
|---|---|---|---|
| 2,804,491 | 8/1957 | May et al. | 260/683.4 |
| 2,939,890 | 6/1960 | Hervert et al. | 260/671 |
| 3,251,902 | 5/1966 | Garwood et al. | 260/683.64 |
| 3,450,644 | 6/1969 | Lanewala et al. | 252/416 |
| 3,467,728 | 9/1969 | Hervert | 260/683.2 |
| 3,549,557 | 12/1970 | Bolton et al. | 252/455 |
| 3,647,916 | 3/1972 | Caesar et al. | 260/683.43 |
| 3,655,813 | 4/1972 | Kirsch et al. | 260/683.43 |
| 3,706,814 | 12/1972 | Kirsch et al. | 260/683.43 |
| 3,738,977 | 6/1973 | Biale | 260/94.9 |
| 3,800,003 | 3/1974 | Sobel | 260/683.49 |
| 3,862,258 | 1/1975 | Huang et al. | 260/683.44 |
| 3,893,942 | 7/1975 | Yang | 585/722 |
| 3,917,738 | 11/1975 | Fenske et al. | 260/683.43 |
| 4,308,414 | 12/1981 | Madgavkar et al. | 585/525 |
| 4,365,105 | 12/1982 | Morganson et al. | 585/525 |
| 4,384,161 | 5/1983 | Huang | 585/722 |
| 4,394,296 | 7/1983 | Madgavkar et al. | 252/433 |
| 4,429,177 | 1/1984 | Morganson et al. | 585/525 |
| 4,918,255 | 4/1990 | Chou et al. | 585/722 |
| 4,954,325 | 9/1990 | Rubin et al. | 423/328 |
| 4,992,615 | 2/1991 | Huss, Jr. et al. | 585/722 |
| 5,012,033 | 4/1991 | Child et al. | 585/722 |
| 5,073,665 | 12/1991 | Child et al. | 585/722 |

OTHER PUBLICATIONS

"Modern Alkylation" by Lyle F. Albright, pub. in Nov. 12 and 26, 1990 issues of *Oil and Gas Journal*.

*Primary Examiner*—Asok Pal
*Attorney, Agent, or Firm*—Alexander J. McKillop; Dennis P. Santini; Robert B. Furr, Jr.

[57] ABSTRACT

Process for alkylating an olefin with an isoparaffin comprising contacting an olefin-containing feed with an isoparaffin-containing feed with a crystalline microporous material under alkylation conversion conditions including temperature at least equal to the critical temperature of the principal component of the feed and pressure at least equal to the critical pressure of the principal component of the feed.

3 Claims, 7 Drawing Sheets

SOLID CATALYZED SUPERCRITICAL ISOPARAFFIN-OLEFIN ALKYLATION PROCESS

FIELD OF THE INVENTION

The present invention relates to the art of improving octane rating of gasoline by alkylating an isoparaffin with an olefin stream. More particularly, the invention relates to a method for increasing the longevity of a solid catalyst in an isoparaffin-olefin alkylation process.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

With the increasing demands for octane and the increasing environmental concerns, it has been desirable to develop an alkylation process employing safer, more environmentally acceptable catalyst systems. Specifically, it is desirable to provide an industrially viable alternative to the currently used hydrofluoric and sulfuric acid alkylation processes. Consequently, substantial efforts have been made to develop a viable isoparaffin-olefin alkylation process which avoids the environmental and safety problems associated with sulfuric and hydrofluoric acid alkylation while retaining the alkylate quality and reliability characteristic of these well-known processes. Research efforts have been directed toward solid as well as liquid alkylation catalyst systems, as reflected in the following references.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$-$C_3$ olefins using certain crystalline aluminosilicate zeolite catalysts in a fixed-, moving- or fluidized bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkylation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio. According to the patent, problems arise in the use of solid catalyst in that they appear to age rapidly and cannot perform effectively at high olefin space velocity and the patent teaches the above solution to rectify the problem utilizing a zeolite alkylation catalyst.

The article entitled "Fixed Bed Catalytic Process to Produce Synthetic Lubricants from Decene-1", IND. ENG. CHEM. PROD. RES. DEV., Vol. 22, No. 4 (1983) teaches oligomerizing olefin to produce fluids with lubricating properties using a silica-BF$_3$-water catalyst. The authors further teach that with this system much of the BF$_3$ can be recycled to minimize BF$_3$ consumption and disposal problems. The reference teaches that water is a necessary component of the system and that in its absence a BF$_3$-silica catalyst rapidly deactivates.

In U.S. Pat. No. 4,308,414, an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 4,429,177 further relates to a method for making lubricating oil utilizing a catalyst comprising boron trifluoride, a minute amount of elemental oxygen and a particulate absorbent material such as silica.

U.S. Pat. No. 4,365,105 also relates to oligomerizing an olefin in the presence of three-component catalyst used in making lubricating oils which comprises a particular silica absorbent with boron trifluoride and water absorbed on the silica.

U.S. Pat. No. 4,394,296 relates to a three-component catalyst used in making lubricating oils which comprises a particular silica absorbent with boron trifluoride and water absorbed on the silica.

U.S. Pat. No. 2,939,890 discloses a process for alkylating an aromatic hydrocarbon with an olefin-acting compound at alkylation conditions in the presence of an alkylation catalyst comprising boron trifluoride-modified alumina. Subsequently, U.S. Pat. No. 3,131,230 discloses the importance of the presence of small amounts of water for maintaining catalyst activity. Both of these patents are limited to aromatic alkylation processes.

U.S. Pat. No. 2,804,491 relates to an isoparaffin-olefin alkylation to make gasoline at temperatures between −20° and 150° F. utilizing a two-component catalyst comprising essentially excess BF$_3$ with a "silica stabilized gel alumina." No activators are taught.

U.S. Pat. Nos. 3,251,902 and 3,893,942, as well as French Patent 1,593,716 and the article by Kirsh and Potts, DIV. OF PET. CHEM. A.C.S. 15, A109 (1970) address alkylation in the presence of zeolite-based catalyst systems.

U.S. Pat. No. 3,467,728 relates to a process for isomerizing olefinic hydrocarbon, such as 1-butene or 1-pentene by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

The two-part article "Modern Alkylation", by Lyle F. Albright, published in the Nov. 12 and 26, 1990 issues of the *Oil and Gas Journal* summarizes the present state of H$_2$SO$_4$ and HF alkylation technology.

Thus while it would be desirable to substitute a solid alkylation catalyst for the liquid catalysts described above, solid catalysts have not proven in the past to be commercially viable alternatives to liquid acid catalysts due to problems with catalyst longevity and alkylate product quality.

SUMMARY OF THE INVENTION

The present invention includes a process for alkylating an olefin with an isoparaffin comprising contacting an olefin-containing feed with an isoparaffin-containing feed with a crystalline microporous material under alkylation conversion conditions including temperature at least equal to the critical temperature of the principal component of the feed and pressure at least equal to the critical pressure of the principal component of the feed. In a preferred embodiment, the fresh crystalline microporous material contacts the mixed isoparaffin-olefin feed only under process conditions which are at least equal to the critical temperature and pressure of the principal component of the feed.

DETAILED DESCRIPTION

Figure 1:
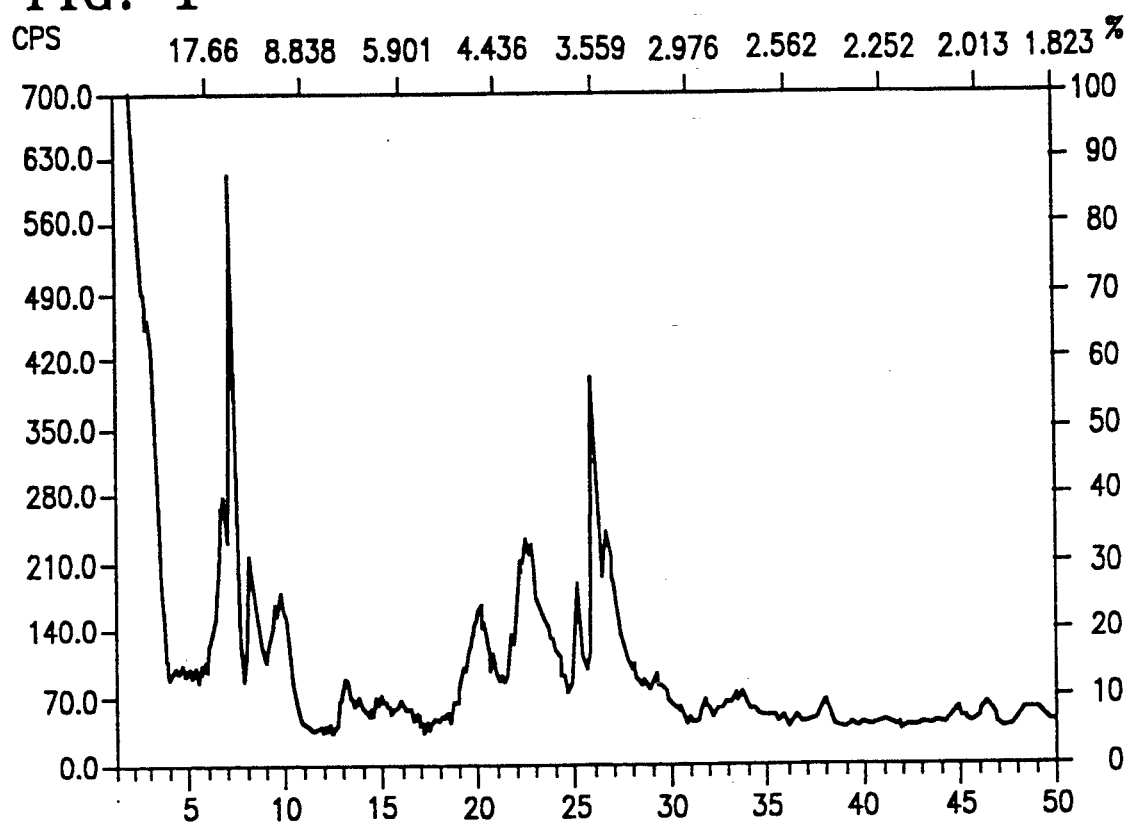
FIG. 1 is an X-ray diffraction pattern of an as-synthesized form of a layered material which may be swollen and pillared.

The process of the invention converts a feedstock containing at least one isoparaffin having from 4 to 8 carbon atoms and at least one olefin having from 2 to 12 carbon atoms to a product stream containing a higher molecular weight isoparaffin. The process further includes a process for alkylating an olefin with an isoparaffin comprising contacting an olefin-containing feed with an isoparaffin-containing feed with a crystalline microporous material under alkylation conversion conditions including temperature at least equal to the critical temperature of the principal component of the feed and pressure at least equal to the critical pressure of the principal component of the feed. Contacting the isoparaffin-olefin feed with the crystalline microporous material under supercritical conditions and avoiding contact between the feed and the crystalline microporous material under subcritical conditions has been found to prolong the useful catalytic life of the crystalline microporous material.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

Isoparaffin:olefin ratios in the reactor feed typically range from about 1.5:1 to about 100:1 to produce a high-octane isobutane:butene alkylate product at industrially useful yields. Higher isoparaffin:olefin ratios may also be used, however limited availability of produced isoparaffin within the refinery coupled with the relatively high cost of purchased isoparaffin favor isoparaffin:olefin ratios within the ranges listed above.

Process Conditions

The present alkylation process is suitably conducted at temperatures from about 275° F. up to about 700° F., preferably from about 300° F. to about 600° F. Operating temperature must exceed the critical temperature of the principal component in the feed. The term "principal component" as used herein is defined as the component of highest concentration in the feedstock. For example, isobutane is the principal component in a feedstock consisting of isobutane and 2-butene in isobutane:2-butene weight ratio of 50:1.

Operating pressure is similarly controlled to maintain the principal component of the feed in the supercritical state, and is suitably from about 300 to about 1500 psig, preferably from about 400 to about 1000 psig. Critical constants for selected useful feedstock components are shown below in Table 38. In a preferred embodiment, the operating temperature and pressure remains above the critical value for the principal feed component during the entire process run, including the first contact between fresh catalyst and fresh feed.

Hydrocarbon flow through the alkylation zone containing the catalyst is typically controlled to provide olefin weight hourly space velocity (WHSV) sufficient to convert about 99 percent by weight of fresh olefin to alkylate product. Typical WHSV values fall within the range of from about 0.01 to about 10 $hr^{-1}$.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

Catalysts

Catalysts useful in the present invention include porous crystalline solids and layered materials. The non-zeolitic inorganic oxide of the solid catalyst may be selected from among the diverse inorganic oxides, examples of which include, but are not limited to, alumina, silica, boria, oxides of phorphorus, titanium dioxide, zirconium dioxide, chromia, zinc oxide, magnesia, calcium oxide, silica-alumina, silica-magnesia, silica-alumina-magnesia, silica-alumina-zirconia, as well as the naturally occurring inorganic oxides of various states of purity such as bauxite, clay, diatomaceous earth, merely to name a few. The preferred inorganic oxides are amorphous silicon dioxide and aluminum oxide. Isoparaffin/olefin alkylation in the presence of a non-zeolitic inorganic oxide and a Lewis acid is taught in U.S. Pat. No. 4,918,255 to Chou et al., as well as in U.S. Pat. No. 4,956,518 to Child et al. The entire disclosures of both are incorporated herein by reference.

Zeolite catalysts which are useful in the alkylation process of this invention include those possessing a Constraint Index of not greater than about 12. The method by which Constraint Index is determined is described fully in U.S. Pat. No. 4,016,218, incorporated herein by reference for details of the method. Constraint Index (CI) values for some typical zeolites including some which are suitable as catalysts in the aromatic alkylation process of this invention are:

|  | CI (at test temperature) |
| --- | --- |
| ZSM-4 | 0.5 (316° C.) |
| ZSM-5 | 6-8.3 (371° C.-316° C.) |
| ZSM-11 | 5-8.7 (371° C.-316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6-2.0 (316° C.-399° C.) |

The above-described Constraint Index is an important and even critical definition of those zeolites which are useful in the aromatic alkylation process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood to those skilled in the art that the CI as utilized herein, while affording a highly useful means for characterizing the zeolites of interest, is approximate taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

Large pore crystalline molecular sieves which can be used in the present invention include those which absorb 2,2,4-trimethylpentane. Representative large pore crystalline molecular sieves include, for example, the following zeolites: ZSM-3, ZSM-4, ZSM-12, ZSM-18, ZSM-20, zeolite L, mordenite, faujasite, zeolite Y, MCM-22 and the rare earth metal-containing forms of the above-listed zeolites. Zeolite Beta can also be used in the present invention, although it is understood that zeolite Beta may exhibit characteristics of a medium-pore zeolite or a large-pore zeolite depending upon process conditions. Isoparaffin/olefin alkylation in the presence of a large pore zeolite is taught in U.S. Pat. No. 4,918,255 to Chou et al., cited above, as well as in allowed U.S. patent application Ser. No. 425,497, filed Oct. 17, 1989, which is a Continuation of Ser. No. 219,130, filed Jul. 15, 1988, now abandoned. U.S. Pat. Nos. 4,962,256 and 4,992,606 also teach crystalline microporous materials which are useful in the present process.

Some zeolite catalysts which are useful in the process of this invention include zeolites ZSM-4, ZSM-12, ZSM-20, ZSM-35, ZSM-48, ZSM-50, MCM-22, PSH-3, TMA offretite, TEA mordenite, clinoptilolite, mordenite, REY and zeolite Beta. Of these, zeolites ZSM-12, MCM-22 and Beta are preferred and zeolite MCM-22 is particularly preferred.

Zeolite ZSM-4 is taught in British Patent No. 1,117,568; ZSM-12 in U.S. Pat. No. 3,832,449: ZSM-20 in U.S. Pat. No. 3,972,983; ZSM-35 in U.S. Pat. No. 4,016,245; ZSM-48 in U.S. Pat. No. 4,397,827; ZSM-50 in U.S. Pat. No. 4,640,849; Beta in U.S. Pat. No. 3,308,069, and PSH-3 in U.S. Pat. No. 4,439,409, each incorporated herein by reference.

Zeolite MCM-22, and in particular its x-ray diffraction pattern, together with a detailed description of its synthesis, are set forth in U.S. Pat. No. 4,954,325 which is incorporated by reference as if set forth at length herein.

The large pore zeolite selected for use in the present alkylation process generally exhibits an alpha value over a wide range of from less than about 1 to more than 1000. The index "Alpha value" measures zeolite acidic functionality and is described in detail in 61 *J. Catalysis* 395 (1980), which description is incorporated by reference as if set forth at length herein.

Zeolites of low acidity, i.e. zeolites having alpha values of less than about 200, can be achieved by a variety of techniques including (a) synthesizing a zeolite with a high silica:alumina ratio, (b) steaming, (c) steaming followed by dealuminization, and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g. at from about 350° to about 750° F. with pressure of from about 10 to about 200 atmospheres. Specific details of several steaming procedures are disclosed in U.S. Pat. Nos. 4,325,994; 4,374,296; and 4,418,235, which patents are incorporated as if set forth at length herein. In addition to, or apart from these steaming procedures, the surface acidity of the zeolite can be eliminated or reduced by treatment with bulky reagents as described in U.S. Pat. No. 4,520,221, which patent is incorporated herein by reference.

Additional molecular sieves which find utility in conjunction with the present invention include pillared silicates and/or clays; aluminophosphates, e.g. ALPO-5, VPI-5; silicoaluminophosphates, e.g. SAPO-5, SAPO-37, SAPO-31, SAPO-40, SAPO-41; and other metal aluminophosphates. These are variously described in U.S. Pat. Nos. 4,440,871; 4,554,143; 4,567,029; 4,666,875; and 4,742,033.

The layered material MCM-36, as described below, is also a useful catalyst in accordance with the invention. MCM-36 is an oxide material having the X-ray diffraction pattern comprising the following lines:

| d (A) | I/I$_o$ |
|---|---|
| >32.2 | vs |
| 12.13–12.66 | w–s |
| 3.35–3.51 | w–s |

MCM-36 can be prepared using an as-synthesized crystalline oxide material to prepare a precursor to a pillared oxide material, by contacting the as-synthesized material with an organic swelling agent under conditions sufficient to swell the as-synthesized material, thereby forming the precursor. The as-synthesized material has the X-ray diffraction pattern comprising the following lines:

| d (A) | $I/I_o$ |
|---|---|
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.10 | w-m |
| 3.95 ± 0.08 | w-vs |
| 3.56 ± 0.06 | w-m |
| 3.43 ± 0.06 | m-vs |
| 3.36 ± 0.05 | w-s | and the precursor has an X-ray diffraction pattern comprising the following lines:

| d (A) | $I/I_o$ |
|---|---|
| >32.2 | vs |
| 12.41 ± 0.25 | w-s |
| 3.44 ± 0.07 | w-s |

MCM-36 may be prepared from an intermediate material which is crystallized in the presence of, e.g., a hexamethyleneimine directing agent and which, if calcined, without being swollen would be transformed into a material having an X-ray diffraction pattern as shown in Table 1.

TABLE 1

| Interplanar d-Spacing (A) | Relative Intensity, $I/I_o \times 100$ |
|---|---|
| 30.0 ± 2.2 | w-m |
| 22.1 ± 1.3 | w |
| 12.36 ± 0.2 | m-vs |
| 11.03 ± 0.2 | m-s |
| 8.83 ± 0.14 | m-vs |
| 6.86 ± 0.14 | w-m |
| 6.18 ± 0.12 | m-vs |
| 6.00 ± 0.10 | w-m |
| 5.54 ± 0.10 | w-m |
| 4.92 ± 0.09 | w |
| 4.64 ± 0.08 | w |
| 4.41 ± 0.08 | w-m |
| 4.25 ± 0.08 | w |
| 4.10 ± 0.07 | w-s |
| 4.06 ± 0.07 | w-s |
| 3.91 ± 0.07 | m-vs |
| 3.75 ± 0.06 | w-m |
| 3.56 ± 0.06 | w-m |
| 3.42 ± 0.06 | vs |
| 3.30 ± 0.05 | w-m |
| 3.20 ± 0.05 | w-m |
| 3.14 ± 0.05 | w-m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

The values in this Table and like tables presented hereinafter were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables 1-8, the relative intensities are given in terms of the symbols w=weak, m=medium, s=strong and vs=very strong. In terms of intensities, these may be generally designated as follows:

| w = | 0–20 |
|---|---|
| m = | 20–40 |
| s = | 40–60 |
| vs = | 60–100 |

The material having the X-ray diffraction pattern of Table 1 is known as MCM-22 and is described in U.S. Pat. No. 4,954,325, the entire disclosure of which is incorporated herein by reference. This material can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the reaction mixture having a composition, in terms of mole ratios of oxides, within the following ranges:

| Reactants | Useful | Preferred |
|---|---|---|
| $YO_2/X_2O_3$ | 10–80 | 10–60 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In the synthesis method for preparing the material having the X-ray diffraction pattern of Table 1, the source of $YO_2$ must be comprised predominately of solid $YO_2$, for example at least about 30 wt. % solid $YO_2$ in order to obtain the desired crystal product. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method taught in U.S. Pat. No. 4,439,409. If another source of oxide of silicon e.g., Q-Brand (a sodium silicate comprised of about 28.8 wt. % $SiO_2$, 8.9 wt. % $Na_2O$ and 62.3 wt. % $H_2O$) is used, crystallization yields little or none of the crystalline material having the X-ray diffraction pattern of Table 1. Impurity phases of other crystal structures, e.g., ZSM-12, are prepared in the latter circumstance. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the crystalline material having the X-ray diffraction pattern of Table 1 can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

The organic directing agent for use in synthesizing the crystalline material MCM-36 from the above reaction mixture may be hexamethyleneimine which has the following structural formula:

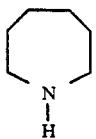

Other organic directing agents which may be used include 1,4-diazacycloheptane, azacyclooctane, aminocyclohexane, aminocycloheptane, aminocyclopentane, N,N,N-trimethyl-1-adamantanammmonium ions, and N,N,N-trimethyl-2-adamantanammmonium ions. In general, the organic directing agent may be selected from the group consisting of heterocyclic imines, cycloalkyl amines and adamantane quaternary ammonium ions.

It should be realized that the reaction mixture components can be supplied by more than one source. The reaction mixture can be prepared either batchwise or continuously. Crystal size and crystallization time of the crystalline material will vary with the nature of the reaction mixture employed and the crystallization conditions.

Synthesis of crystals may be facilitated by the presence of at least 0.01 percent, e.g., o.10 percent or 1 percent, seed crystals (based on total weight) of crystalline product.

The crystalline material having the X-ray diffraction pattern of Table 1 passes through an intermediate stage. The material at this intermediate stage has a different X-ray diffraction pattern than that set forth in Table 1. It has further been discovered that this intermediate material is swellable with the use of suitable swelling agents such as cetyltrimethylammonium compounds, e.g., cetyltrimethylammonium hydroxide. However, when this intermediate material is calcined, even under mild conditions, whereby the swelling agent is removed, the material can no longer be swollen with such swelling agent. By way of contrast it is noted that various layered silicates such as magadiite and kenyaite may be swellable with cetyltrimethylammonium compounds both prior to and after mild calcination.

The present swollen products may have relatively high interplanar distance (d-spacing), e.g., greater than about 6 Angstrom, e.g., greater than about 10 Angstrom and even exceeding 30 Angstrom. These swollen materials may be converted into pillared materials. These pillared materials, particularly silica pillared materials, may be capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance. The material having the X-ray diffraction pattern of Table 1, when intercepted in the swellable, intermediate state, prior to final calcination, may have the X-ray diffraction pattern shown in Table 2.

TABLE 2

| d (A) | I/I$_o$ |
|---|---|
| 13.53 ± 0.2 | m–vs |
| 12.38 ± 0.2 | m–vs |
| 11.13 ± 0.2 | w–s |
| 9.15 ± 0.15 | w–s |
| 6.89 ± 0.15 | w–m |
| 4.47 ± 0.10 | w–m |
| 3.95 ± 0.08 | w–vs |
| 3.56 ± 0.06 | w–m |

TABLE 2-continued

| d (A) | I/I$_o$ |
|---|---|
| 3.43 ± 0.06 | m–vs |
| 3.36 ± 0.05 | w–s |

An X-ray diffraction pattern trace for an example of such an as-synthesized, swellable material is shown in FIG. 1. A particular example of such an as-synthesized, swollen material is the material of Example 1 of the aforementioned U.S. Pat. No. 4,954,325. This material of Example 1 of U.S. Pat. No. 4,954,325 has the X-ray diffraction pattern given in the following Table 3.

TABLE 3

| 2 Theta | d (A) | I/I$_o$ × 100 |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Taking into account certain modifications, this swellable material may be swollen and pillared by methods generally discussed in the aforementioned U.S. Pat. No. 4,859,648, the entire disclosure of which is expressly incorporated herein be reference. The present modifications are discussed hereinafter and include the selection of proper swelling pH and swelling agent.

Upon being swollen with a suitable swelling agent, such as a cetyltrimethylammonium compound, the swollen material may have the X-ray diffraction pattern as shown in Table 4.

TABLE 4

| d (A) | I/I$_o$ |
|---|---|
| >32.2 | vs |
| 12.41 ± 0.25 | w–s |
| 3.44 ± 0.07 | w–s |

The X-ray diffraction pattern of this swollen material may have additional lines with a d(A) spacing less than the line at 12.41±0.25, but none of the additional lines have an intensity greater than the line at the d(A) spacing of 12.41±0.25 or at 3.44±0.07, whichever is more intense. More particularly, the X-ray diffraction pattern of this swollen material may have the lines shown in the following Table 5.

TABLE 5

| d (A) | I/I₀ |
|---|---|
| >32.2 | vs |
| 12.41 ± 0.25 | w-s |
| 11.04 ± 0.22 | w |
| 9.28 ± 0.19 | w |
| 6.92 ± 0.14 | w |
| 4.48 ± 0.09 | w-m |
| 3.96 ± 0.08 | w-m |
| 3.57 ± 0.07 | w-m |
| 3.44 ± 0.07 | w-s |
| 3.35 ± 0.07 | w |

Even further lines may be revealed upon better resolution of the X-ray diffraction pattern. For example, the X-ray diffraction pattern may have additional lines at the following d(A) spacings (intensities given in parentheses): 16.7±4.0 (w-m); 6.11±0.24 (w); 4.05±0.08 (w); and 3.80±0.08 (w).

In the region with d<9 A, the pattern for the swollen material is essentially like the one given in Table 2 for the unswollen material, but with the possibility of broadening of peaks.

Figure 2:
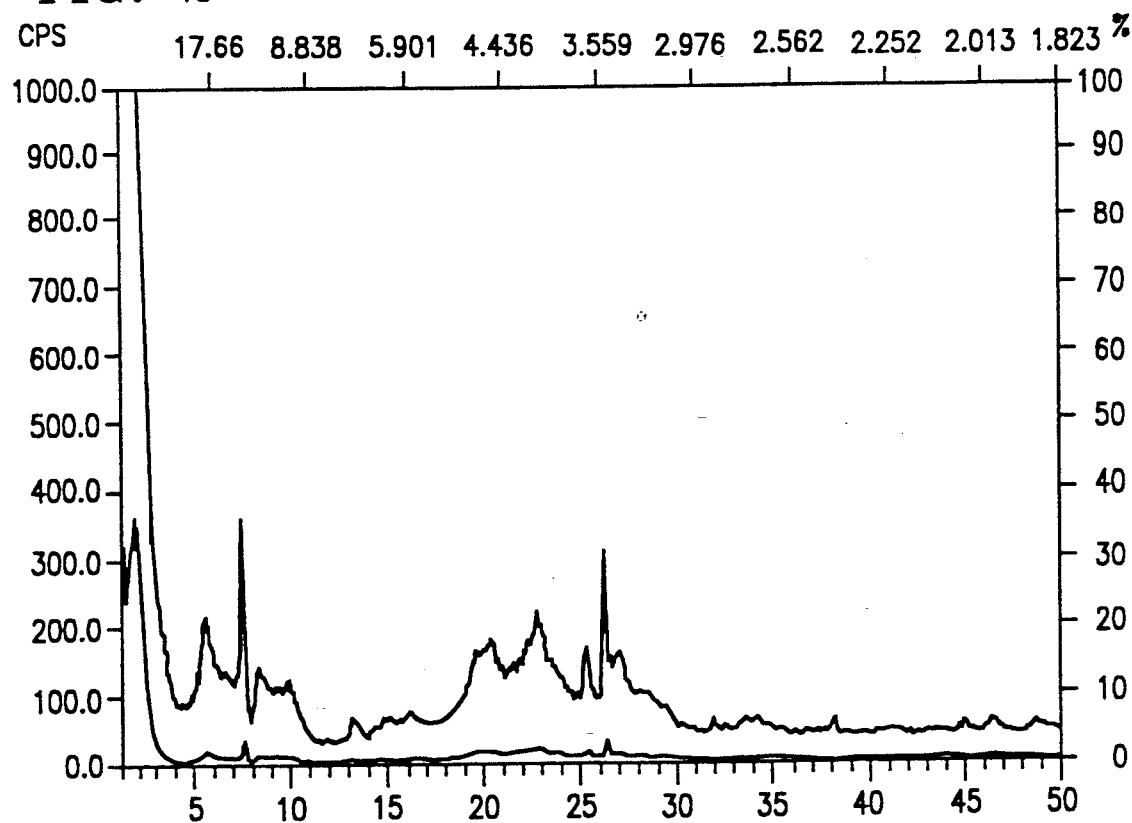
FIG. 2 is an X-ray diffraction pattern of a swollen form of the material having the X-ray diffraction pattern shown in FIG. 1.

An X-ray diffraction pattern trace for an example of such a swollen material is shown in FIG. 2. The upper profile is a 10-fold magnification of the lower profile in FIG. 2.

Upon being pillared with a suitable polymeric oxide, such as polymeric silica, the swollen material having the X-ray diffraction pattern shown in Table 4 may be converted into a material having the X-ray diffraction pattern shown in Table 6.

TABLE 6

| d (A) | I/I₀ |
|---|---|
| >32.2 | vs |
| 12.38 ± 0.25 | w-m |
| 3.42 ± 0.07 | w-m |

The X-ray diffraction pattern of this pillared material may have additional lines with a d(A) spacing less than the line at 12.38±0.25, but none of the additional lines have an intensity greater than the line at the d(A) spacing of 12.38±0.25 or 3.42±0.07, whichever is more intense. More particularly, the X-ray diffraction pattern of this pillared material may have the lines shown in the following Table 7.

TABLE 7

| d (A) | I/I₀ |
|---|---|
| >32.2 | vs |
| 12.38 ± 0.25 | w-m |
| 10.94 ± 0.22 | w-m |
| 9.01 ± 0.18 | w |
| 6.88 ± 0.14 | w |
| 6.16 ± 0.12 | w-m |
| 3.93 ± 0.08 | w-m |
| 3.55 ± 0.07 | w |
| 3.42 ± 0.07 | w-m |
| 3.33 ± 0.07 | w-m |

Even further lines may be revealed upon better resolution of the X-ray diffraction pattern. For example, the X-ray diffraction pattern may have additional lines at the following d(A) spacings (intensities given in parentheses): 5.59±0.11 (w); 4.42±0.09 (w); 4.11±0.08 (w); 4.04±0.08 (w); and 3.76±0.08 (w).

Figure 3:
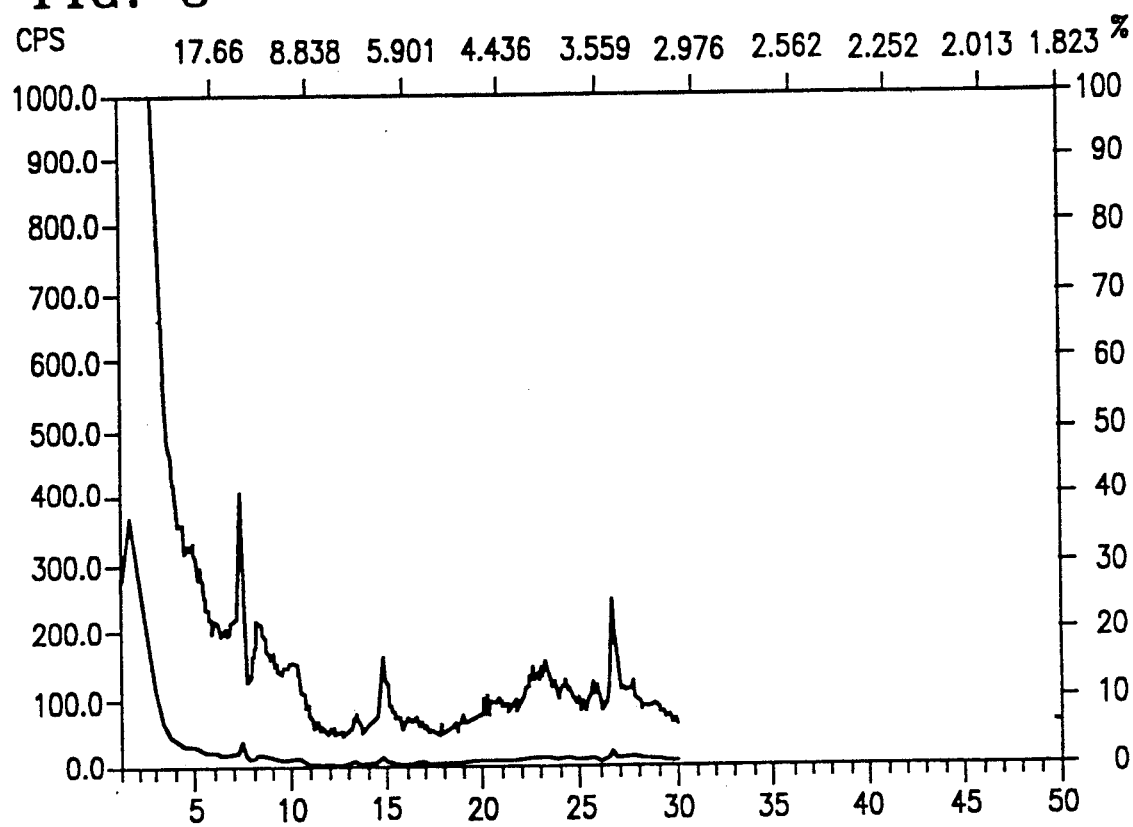
FIG. 3 is an X-ray diffraction pattern of the pillared form of the layered material having the X-ray diffraction pattern shown in FIG. 1.

An X-ray diffraction pattern trace for an example of such a pillared material is given in FIG. 3. The upper profile is a 10-fold magnification of the lower profile in FIG. 3.

If the material swollen with a suitable swelling agent is calcined without prior pillaring another material is produced. For example, if the material which is swollen but not pillared is calcined in air for 6 hours at 540° C., a very strong line at a d(A) spacing of greater than 32.2 will no longer be observed. By way of contrast, when the swollen, pillared material is calcined in air for 6 hours at 540° C., a very strong line at a d(A) spacing of greater than 32.2 will still be observed, although the precise position of the line may shift.

An example of a swollen, non-pillared material, which has been calcined, has the pattern as shown in Table 8.

TABLE 8

| 2 Theta | d (A) | I/I₀ × 100 | |
|---|---|---|---|
| 3.8 | 23.3 | 12 | |
| 7.02 | 12.59 | 100 | |
| 8.02 | 11.02 | 20 | |
| 9.66 | 9.16 | 14 | |
| 12.77 | 6.93 | 7 | |
| 14.34 | 6.18 | 45 | |
| 15.75 | 5.63 | 8 | |
| 18.19 | 4.88 | 3 | |
| 18.94 | 4.69 | 3 | |
| 19.92 | 4.46 | 13 | broad |
| 21.52 | 4.13 | 13 | shoulder |
| 21.94 | 4.05 | 18 | |
| 22.55 | 3.94 | 32 | |
| 23.58 | 3.77 | 16 | |
| 24.99 | 3.56 | 20 | |
| 25.94 | 3.43 | 61 | |
| 26.73 | 3.33 | 19 | |
| 31.60 | 2.831 | 3 | |
| 33.41 | 2.682 | 4 | |
| 34.62 | 2.591 | 3 | broad |
| 36.36 | 2.471 | 1 | |
| 37.81 | 2.379 | 4 | |

The X-ray powder pattern shown in Table 8 is similar to that shown in Table 1 except that most of the peaks in Table 8 are much broader than those in Table 1.

Figure 4:
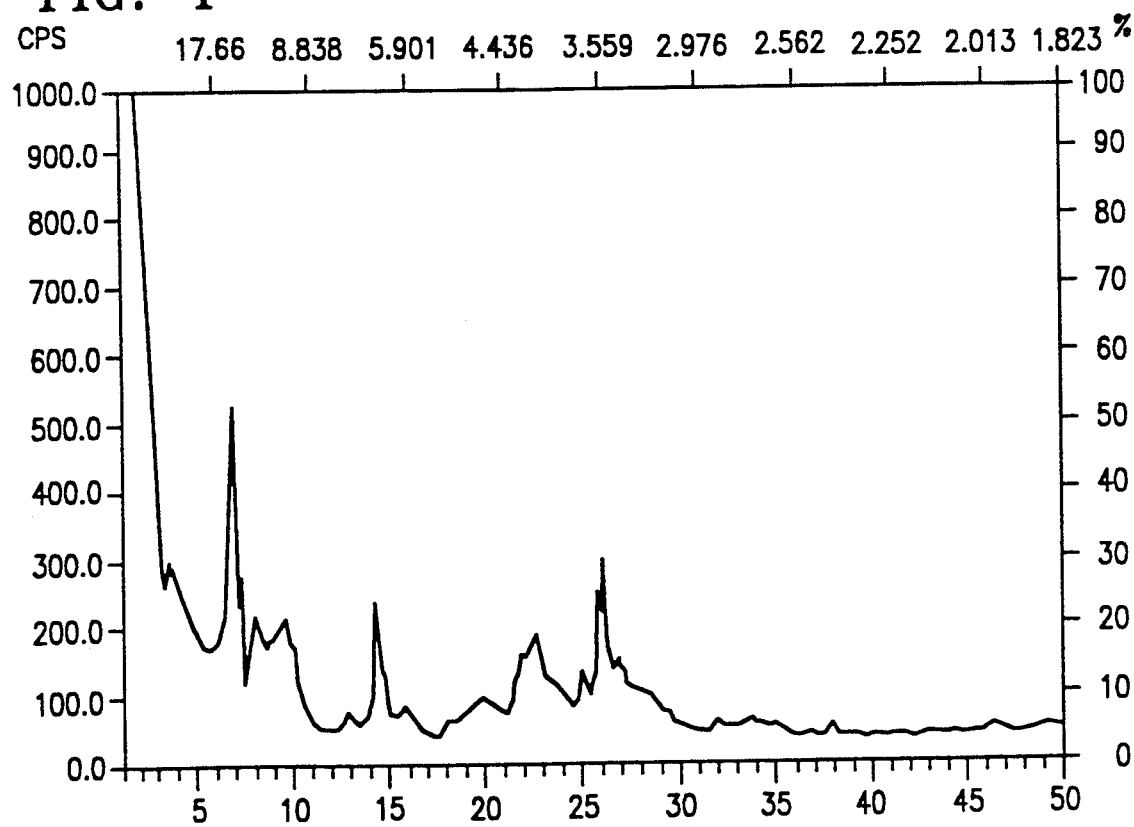
FIG. 4 is an X-ray diffraction pattern of the calcined form of the swollen material having the X-ray diffraction pattern shown in FIG. 2.
Figure 5A:
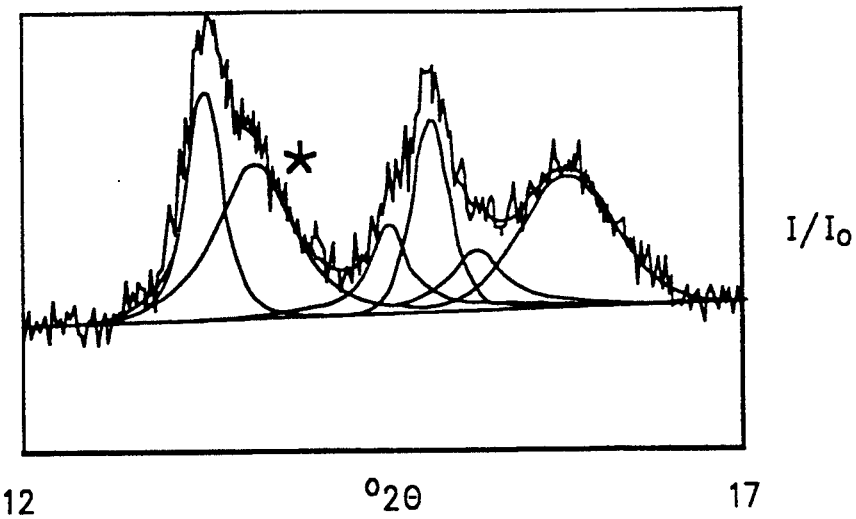
FIG. 5a shows a segment of the X-ray diffraction pattern of the as-synthesized precursor of MCM-22 from a repeat of Example 1 of U.S. Pat. No. 4,954,325.
Figure 5B:
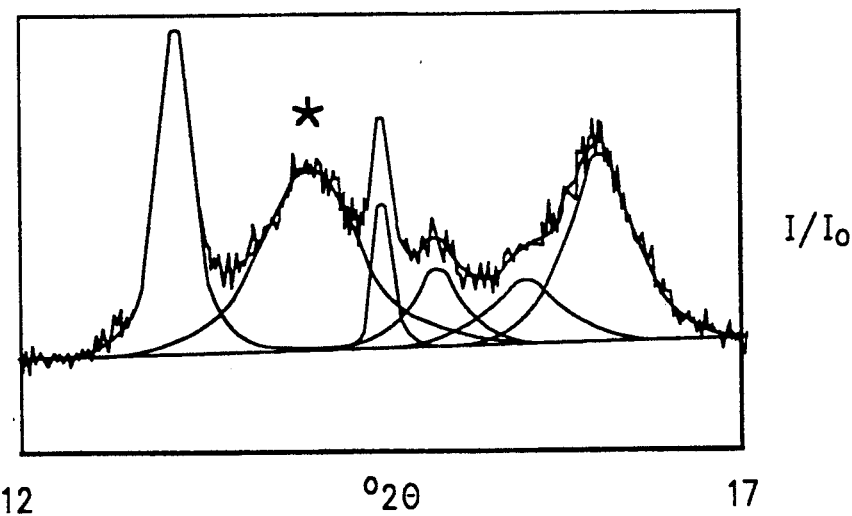
FIG. 5b shows a segment of the X-ray diffraction pattern of the as-synthesized crystalline material product of Example 19.
Figure 5C:
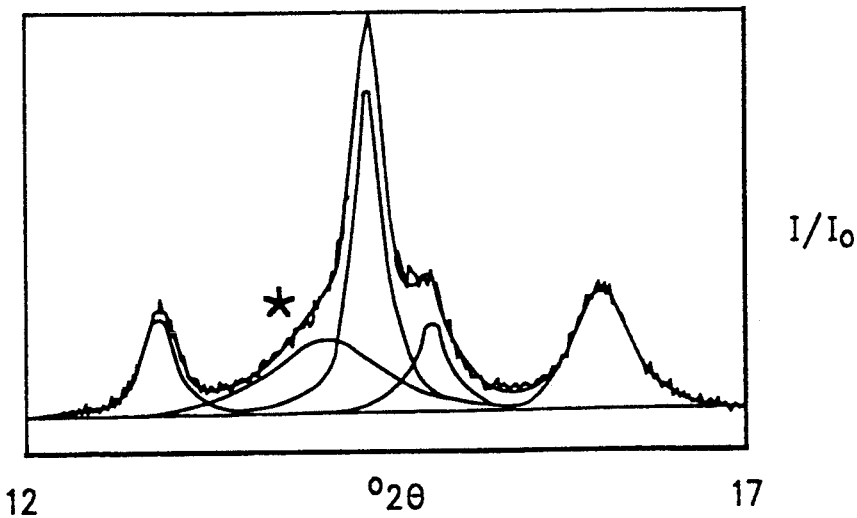
FIG. 5c shows a segment of the X-ray diffraction pattern of the calcined MCM-22 from a repeat of Example 1 of U.S. Pat. No. 4,954,325.

An X-ray diffraction pattern trace for an example of the calcined material corresponding to Table 8 is given in FIG. 4.

As mentioned previously, the calcined material corresponding to the X-ray diffraction pattern of Table 1 is designated MCM-22. For the purposes of the present disclosure, the pillared material corresponding to the X-ray diffraction pattern of Table 6 is designated herein as MCM-36. The swollen material corresponding to the X-ray diffraction pattern of Table 4 is designated herein as the swollen MCM-22 precursor. The as-synthesized material corresponding to the X-ray diffraction pattern of Table 2 is referred to herein, simply, as the MCM-22 precursor.

The layers of the swollen material of this disclosure may have a composition involving the molar relationship:

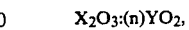

$X_2O_3:(n)YO_2,$ wherein X is a trivalent element, such as aluminum, boron, iron and/or gallium, preferably aluminum, Y is a tetravalent element such as silicon and/or germanium, preferably silicon, and n is at least about 5, usually from about 10 to about 150, more usually from about 10 to about 60, and even more usually from about 10 to about 40.

To the extent that the layers of the swollen MCM-22 precursor and MCM-36 have negative charges, these negative charges are balanced with cations. For example, expressed in terms of moles of oxides, the layers of the swollen MCM-22 precursor and MCM-36 may have a ratio of 0.5 to 1.5 $R_2O:X_2O_3$, where R is a monovalent cation or 1/m of a cation of valency m.

The pillared material of the present disclosure adsorbs significant amounts of commonly used test adsorbate materials, i.e., cyclohexane, n-hexane and water. Adsorption capacities for the pillared material, especially the silica pillared material, of the present invention may range at room temperature as follows:

| Adsorbate | Capacity, Wt. Percent |
|---|---|
| n-hexane | 17–40 |
| cyclohexane | 17–40 |
| water | 10–40 | wherein cyclohexane and n-hexane sorption are measured at 20 Torr and water sorption is measured at 12 Torr.

The swellable material, used to form the swollen material may be initially treated with a swelling agent. Such swelling agents are materials which cause the swellable layers to separate by becoming incorporated into the interspathic region of these layers. The swelling agents are removable by calcination, preferably in an oxidizing atmosphere, whereby the swelling agent becomes decomposed and/or oxidized.

Suitable swelling agents may comprise a source of organic cation, such as quaternary organoammonium or organophosphonium cations, in order to effect an exchange of interspathic cations. Organoammonium cations, such as n-octylammonium, showed smaller swelling efficiency than, for example, cetyltrimethylammonium. A pH range of 11 to 14, preferably 12.5 to 13.5 is generally employed during treatment with the swelling agent.

The as-synthesized material is preferably not dried prior to being swollen. This as-synthesized material may be in the form of a wet cake having a solids content of less than 30% by weight, e.g., 25 wt % or less.

The foregoing swelling treatment results in the formation of a layered oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. When contact of the layered oxide with the swelling agent is conducted in aqueous medium, water is trapped between the layers of the swollen species.

The organic-swollen species may be treated with a compound capable of conversion, e.g., by hydrolysis and/or calcination, to pillars of an oxide, preferably to a polymeric oxide. Where the treatment involves hydrolysis, this treatment may be carried out using the water already present in organic-swollen material. In this case, the extent of hydrolysis may be modified by varying the extent to which the organic-swollen species is dried prior to addition of the polymeric oxide precursor.

It is preferred that the organic cation deposited between the layers be capable of being removed from the pillared material without substantial disturbance or removal of the interspathic polymeric oxide. For example, organic cations such as cetyltrimethylammonium may be removed by exposure to elevated temperatures, e.g., calcination, in nitrogen or air, or by chemical oxidation preferably after the interspathic polymeric oxide precursor has been converted to the polymeric oxide pillars in order to form the pillared layered product.

These pillared layered products, especially when calcined, exhibit high surface area, e.g., greater than 500 $m^2/g$, and thermal and hydrothermal stability making them highly useful as catalysts or catalytic supports, for hydrocarbon conversion processes, for example, alkylation.

Insertion of the organic cation between the adjoining layers serves to physically separate the layers in such a way as to make the layered material receptive to the interlayer addition of a polymeric oxide precursor. In particular, cetyltrimethylammonium cations have been found useful. These cations are readily incorporated within the interlayer spaces of the layered oxide serving to prop open the layers in such a way as to allow incorporation of the polymeric oxide precursor. The extent of the interlayer spacing can be controlled by the size of the organoammonium ion employed Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds, e.g., alkoxides, of the desired elements of the pillars may be utilized as the precursors. Suitable polymeric silica precursor materials include tetraalkylsilicates, e.g., tetrapropylorthosilicate, tetramethylorthosilicate and, most preferably, tetraethylorthosilicate. Suitable polymeric silica precursor materials also include quaternary ammonium silicates, e.g., tetramethylammonium silicate (i.e. TMA silicate). Where the pillars also include polymeric alumina, a hydrolyzable aluminum compound can be contacted with the organic "propped" species before, after or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particular procedures for intercalating layered materials with metal oxide pillars are described in U.S. Pat. Nos. 4,831,005; 4,831,006; and 4,929,587. The entire disclosures of these patents are expressly incorporated herein by reference. U.S. Pat. No. 4,831,005 describes plural treatments with the pillar precursor. U.S. Pat. No. 4,929,587 describes the use of an inert atmosphere, such as nitrogen, to minimize the formation of extralaminar polymeric oxide during the contact with the pillar precursor. U.S. Pat. No. 4,831,006 describes the use of elevated temperatures during the formation of the pillar precursor.

The resulting pillared products exhibit thermal stability at temperatures of 450° C. or even higher as well as substantial sorption capacities (as much as 17 to 40 wt % for $C_6$ hydrocarbon). The pillared products may possess a basal spacing of at least about 32.2Å and surface areas greater than 500 $m^2/g$.

The layered materials described herein can optionally be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition, impregnated therein or intimately physically admixed therewith. Such component can be impregnated in, or on, the layered material such as, for example, by, in the case of platinum, treating the layered material with a solution containing a platinum metal-containing ion. Thus, suitable platinum compounds for this purpose include chloroplatinic acid, platinous chloride and various compounds containing the platinum amine complex.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience.

When the swollen layered material described herein is calcined, without first being contacted with a pillaring material or a pillar precursor, the layers collapse and condense upon one another. These collapsed and condensed layers are not swellable and are apparently chemically linked to one another by covalent bonds. However, the layers of the collapsed and condensed swollen materials tend to be stacked upon one another in a disordered fashion. This disordered stacking of layers is consistent with the broadening of peaks as discussed herein with reference to Table 5 in comparison with the sharper peaks of Table 1.

The swollen materials of the present disclosure are useful as intermediates for preparing the pillared and calcined, swollen materials described herein with particular reference to Table 4 (pillared material) and Table 5 (calcined, swollen material). These pillared and calcined, swollen materials are useful as catalysts, catalyst supports and sorbents. The present swollen materials are also useful as catalysts for processes, wherein these swollen materials are converted into calcined materials, in situ, by heat associated with the processes.

Prior to its use in catalytic processes described herein, the layered material catalyst is preferably dehydrated, at least partially. This dehydration can be done by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the layered material in a vacuum, but a longer time is required to obtain a sufficient amount of dehydration.

The layered material catalyst can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the layered material can be extruded before drying or partially dried and then extruded.

It may be desired to incorporate the layered material with another material which is resistant to the temperatures and other conditions employed in the catalytic processes described herein. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with layered material, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with layered materials include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with layered materials also include inorganic oxides, notably alumina.

In addition to the foregoing materials, the layered materials can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of finely divided layered materials and inorganic oxide matrix vary widely, with the layered material content ranging from about 1 to about 90 percent by weight and more usually, particularly when the composite is prepared in the form of beads, in the range of about 2 to about 80 weight of the composite.

Alpha Values are reported hereinafter for various materials. It is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test preferably include a constant temperature of 538° C. and a variable flow rate as described in detail in the *Journal of Catalysis*, Vol. 61, p. 395.

MCM-36, especially when the layers thereof are composed of an aluminosilicate, may be a very catalytically active material. By way of contrast, other layered materials, such as clays, magadiite, kenyaite, and titanates, in pillared form are much less catalytically active than the very catalytically active forms of the pillared layered oxide, MCM-36. One measure of the catalytic activity of MCM-36 is the Alpha Value for MCM-36. Various catalytically active forms of MCM-36 may have Alpha Values in excess of 10, e.g., 50 or greater. Particularly catalyticaly active forms of MCM-36 comprise those with aluminosilicate layers, these layers having a silica to alumina molar ratio of 300 or less.

Another distinguishing feature of MCM-36, relative to other pillared layered oxides, is the porosity of the layers of MCM-36. Although other pillared oxide materials, such as pillared clays and the pillared materials, e.g., pillared silicates and titanates, discussed in the aforementioned U.S. Pat. No. 4,859,648, have considerable porosity as a result of open interspathic regions, the individual layers of these materials are relatively dense, lacking pore windows formed by 8 or more oxygen atoms. On the other hand, the layers of MCM-36 would appear to have continuous channels having pore windows formed by rings of at least 8 oxygen atoms. More particularly, these pore windows in the layers of MCM-36 would appear to be formed by rings of 10 oxygen atoms. As indicated by argon physisorption measurements, the channels in the layers of MCM-36 have an effective pore diameter of greater than about 5 Angstroms.

Various crystallites from the Examples which follow were examined by transition electron microscopy (TEM).

EXAMPLE 1

This Example describes the synthesis of a material which may be swollen and pillared. Water, sodium hydroxide, sodium aluminate, silica (Ultrasil), and hexamethyleneimine (HMI) were combined in the following ratios:

2.5 Na$_2$O: Al$_2$O$_3$: 30 SiO$_2$:10 HMI: 580 H$_2$O.

The reaction mixture was heated in an autoclave to 143° C. for 96 hours. The X-ray diffraction pattern for this material is shown pictorially in FIG. 1.

EXAMPLE 2

A mixture of a 29 % solution of cetyltrimethylammonium (N,N,N-trimethyl-1-hexadecanaminium) hydroxide, 40% tetrapropylammonium hydroxide and wet cake of Example 1 (20% solids) in the relative weight ratio 105:33:27, respectively, was heated in an autoclave at 105° C. with stirring for 42 hours. The solid product was isolated by decantation and filtration, and the wet cake was washed twice by mixing with water and filtration. The swollen material had the X-ray diffraction pattern given in the following Table 9.

TABLE 9

| 2 Theta | d (A) | I/I$_o$ × 100 |
|---|---|---|
| 1.6 | 55.2 | 100 |
| 4.88 | 18.1 | 2 |
| 6.38 | 13.85 | 3 |
| 7.15 | 12.36 | 21 |
| 7.96 | 11.11 | 6 |
| 9.47 | 9.34 | 4 |
| 12.81 | 6.91 | 2 |
| 14.56 | 6.08 | 1 |
| 19.99 | 4.44 | 9 |
| 21.44 | 4.14 | 5 |
| 21.88 | 4.06 | 7 |
| 22.44 | 3.96 | 8 |
| 23.35 | 3.81 | 3 |
| 24.91 | 3.57 | 6 |
| 25.90 | 3.44 | 21 |
| 26.53 | 3.36 | 4 |

EXAMPLE 3

The product of Example 2 (24% solids) was combined with a 10% solution of silica in aqueous tetramethylammonium hydroxide (molar ratio TMA:SiO$_2$=0.5) in a weight ratio 1:15. The mixture was heated for 20 hr in the steambox, filtered and air dried. The solid was contacted three times with 1M ammonium nitrate (10 ml per 1 ml of solid) and the final product was obtained upon calcination at 540° C. The pillared, calcined material had the X-ray difraction pattern given in the following Table 10.

TABLE 10

| 2 Theta | d (A) | I/I$_o$ × 100 |
|---|---|---|
| 1.9 | 46.5 | 100 |
| 7.17 | 12.33 | 9.0 |
| 8.13 | 10.87 | 3.1 |
| 9.88 | 8.95 | 1.4 |
| 12.90 | 6.86 | 0.9 |
| 14.41 | 6.15 | 3.7 |
| 16.01 | 5.54 | 0.9 |
| 20.16 | 4.40 | 1.5 |
| 21.12 | 4.21 | 0.9 |
| 21.65 | 4.10 | 1.4 |
| 22.03 | 4.03 | 2.2 |
| 22.67 | 3.92 | 3.1 |
| 23.78 | 3.74 | 1.8 |
| 25.10 | 3.55 | 2.2 |
| 26.08 | 3.42 | 7.8 |
| 26.84 | 3.32 | 2.2 |

EXAMPLE 4

In this case the swelling reagent was prepared by contacting a 29% solution of cetyltrimethylammonium (N,N,N-trimethyl-1-hexadecanaminium) chloride with a hydroxide-for-halide exchange resin (one liter of wet resin with 1.4 milliequivalent/ml exchange capacity per 3 l of the solution). It will be referred to as 29% CTMA-OH.

A mixture of 30 g of the Example 1 wet cake (30% solids) and 150 g of the 29% CTMA-OH solution was reacted in the steambox for 65 hours. The product was isolated by filtration, washed twice with 50 ml of water and air dried overnight yielding 10.6 g of the swollen product. The X-ray diffraction pattern for this swollen material is shown pictorially in FIG. 2. The X-ray diffraction pattern for this swollen material is also given in the following Table 11.

TABLE 11

| 2 Theta | d (A) | $I/I_o \times 100$ | |
|---|---|---|---|
| 1.7 | 52.0 | 100 | |
| 2.8 | 31.6 | 20 | |
| 5.24 | 16.86 | 10 | |
| 5.61 | 15.75 | 6 | |
| 7.13 | 12.40 | 32 | |
| 7.99 | 11.06 | 5 | |
| 9.58 | 9.23 | 3 | |
| 12.81 | 6.91 | 3 | |
| 13.98 | 6.33 | 1 | broad |
| 14.60 | 6.07 | 2 | |
| 15.69 | 5.65 | 2 | |
| 19.60 | 4.53 | 11 | broad |
| 21.29 | 4.17 | 12 | |
| 21.92 | 4.05 | 6 | |
| 22.44 | 3.96 | 10 | |
| 23.27 | 3.82 | 6 | broad shoulder |
| 24.94 | 3.57 | 9 | |
| 25.93 | 3.44 | 26 | |
| 26.60 | 3.35 | 8 | |
| 28.00 | 3.19 | 3 | broad |
| 29.08 | 3.07 | 1 | |
| 31.51 | 2.839 | 2 | |
| 33.09 | 2.707 | 1 | broad |
| 33.75 | 2.656 | 1 | broad |
| 34.70 | 2.585 | 1 | broad |
| 36.30 | 2.475 | 1 | |
| 37.09 | 2.424 | 1 | |
| 37.74 | 2.384 | 3 | |

EXAMPLE 5

This Example describes the pillaring of the swollen material of Example 4. The swollen material (8.6 g) was slurried with 50 g of tetraethylorthosilicate (TEOS) and heated at 80° C. for 24 hours under the stream of nitrogen. After filtration and overnight drying the product (7.15 g) was hydrolyzed in water for 5 hr giving the pillared material (6.6 g) containing 68% solids based upon calcination at 450° C. The X-ray diffraction pattern for this pillared material is shown pictorially in FIG. 3. TEM analysis of crystallites confirmed that the layers remained separated after this pillaring procedure. The X-ray diffraction pattern for this pillared, calcined material is also given in the following Table 12.

TABLE 12

| 2 Theta | d (A) | $I/I_o \times 100$ |
|---|---|---|
| 1.7 | 52.0 | 100 |
| 7.14 | 12.38 | 43.9 |
| 8.02 | 11.02 | 14.3 |
| 9.75 | 9.07 | 7.2 |
| 12.82 | 6.90 | 2.8 |
| 14.36 | 6.17 | 18.9 |
| 15.95 | 5.56 | 1.7 |
| 20.01 | 4.44 | 7.0 |
| 21.57 | 4.12 | 6.1 |
| 21.99 | 4.04 | 9.1 |
| 22.58 | 3.94 | 13.9 |
| 23.65 | 3.76 | 8.7 |
| 25.04 | 3.56 | 11.1 |
| 26.02 | 3.42 | 35.4 |
| 26.71 | 3.34 | 10.2 |
| 31.62 | 2.829 | 2.2 |
| 33.44 | 2.680 | 2.0 |
| 36.42 | 2.467 | 1.1 |
| 37.15 | 2.420 | 0.4 |

TABLE 12-continued

| 2 Theta | d (A) | $I/I_o \times 100$ |
|---|---|---|
| 37.87 | 2.376 | 2.2 |

EXAMPLE 6

This Example describes another embodiment of swelling the material of Example 1 using a different swelling medium. The swelling reagent, was prepared by contacting a solution of cetyltrimethylammonium (N,N,N-trimethyl-1-hexadecanaminium) chloride composed of 50% of the latter, 35% 2-propanol and 15% water, with a hydroxide-for-halide exchange resin (two exchanges using ½ liter of wet resin with 1.4 milliequivalent/ml exchange capacity per 1 l of the solution; 200 ml of ethanol was also added). It will be referred to as 50% CTMA-OH.

300 ml of the slurry containing about 20% of the material of Example 1 was mixed with 300 ml of the 50% CTMA-OH solution. The mixture was heated in a 1 l autoclave for 24 hours at 150° C. with stirring. The product was isolated by filtration, washed twice with 400 ml of water and air dried overnight yielding about 140 g of the swollen product. The X-ray diffraction pattern for this swollen material is given in the following Table 13.

TABLE 13

| 2 Theta | d (A) | $I/I_o \times 100$ | |
|---|---|---|---|
| 1.8 | 49.1 | 100 | |
| 5.18 | 17.06 | 25 | |
| 7.20 | 12.28 | 55 | |
| 8.09 | 10.93 | 9 | |
| 9.60 | 9.21 | 7 | |
| 12.87 | 6.88 | 4 | |
| 14.67 | 6.04 | 3 | |
| 15.80 | 5.61 | 2 | |
| 19.73 | 4.50 | 22 | broad |
| 21.45 | 4.14 | 18 | |
| 22.00 | 4.04 | 5 | |
| 22.52 | 3.95 | 22 | |
| 23.39 | 3.80 | 9 | broad shoulder |
| 25.03 | 3.56 | 19 | |
| 26.02 | 3.42 | 59 | |
| 26.69 | 3.34 | 16 | |
| 29.19 | 3.06 | 3 | |
| 31.60 | 2.831 | 3 | |
| 33.16 | 2.702 | 2 | |
| 36.37 | 2.470 | 2 | |
| 37.02 | 2.428 | 1 | |
| 37.82 | 2.379 | 7 | |

EXAMPLE 7

This Example describes swelling of the material prepared from the synthesis mixture of Example 1 that has been crystallized for 48 hours (see below) rather than 96 hours.

The combination of 504 g of water, 11.4 g of 50% sodium hydroxide, 11.4 g of sodium aluminate (43.5%, 30% Na$_2$O), 64.9 g of silica (Ultrasil) and 34.2 g of hexamethyleneimine was reacted in an autoclave at 143° C. for 48 hours with stirring. The product was filtered and washed thoroughly with water.

500 g of the wet cake material (24% solids) described above was mixed with 3 l of 29% CTMA-OH solution and stirred for 48 hours at room temperature. The swollen product was isolated by filtration, washed twice with 500 ml of water and air dried overnight. The X-ray diffraction pattern for this swollen material is given in the following Table 14.

TABLE 14

| 2 Theta | d (A) | $I/I_o \times 100$ | |
|---|---|---|---|
| 1.7 | 52.0 | 100 | |
| 5.18 | 17.06 | 7.3 | |
| 6.81 | 12.98 | 2.3 | |
| 7.10 | 12.45 | 5.7 | |
| 8.79 | 10.06 | 2.7 | very broad |
| 12.73 | 6.95 | 0.6 | |
| 13.82 | 6.41 | 0.4 | |
| 14.55 | 6.09 | 0.3 | |
| 15.59 | 5.68 | 0.7 | |
| 18.39 | 4.82 | 1.3 | broad shoulder |
| 19.06 | 4.66 | 2.6 | shoulder |
| 19.77 | 4.49 | 4.8 | |
| 21.01 | 4.23 | 3.4 | broad |
| 22.28 | 3.99 | 5.0 | |
| 23.35 | 3.81 | 2.3 | broad shoulder |
| 24.91 | 3.57 | 3.0 | |
| 25.90 | 3.44 | 8.0 | |
| 26.50 | 3.36 | 4.4 | |

EXAMPLE 8

This Example describes pillaring of the swollen material of Example 7. 235 g of the product was ground and combined with 1.4 liter of TEOS and treated by a procedure similar to Example 5. The product contained 65% solids based on calcination at 540° C. A sample of the calcined product was examined by argon physisorption which revealed a dual pore system with diameters of 6.3 Angstroms and about 28 Angstroms.

To determine the pore diameters, a 0.2 gram sample of the product of Example 8 was placed in a glass sample tube and attached to a physisorption apparatus as described in U.S. Pat. No. 4,762,010.

The sample was heated to 300° C. for 3 hours in vacuo to remove adsorbed water. Thereafter, the sample was cooled to 87°K by immersion of the sample tube in liquid argon. Metered amounts of gaseous argon were then admitted to the sample in stepwise manner as described in U.S. Pat. No. 4,762,010, column 20. From the amount of argon admitted to the sample and the amount of argon left in the gas space above the sample, the amount of argon adsorbed can be calculated. For this calculation, the ideal gas law and the calibrated sample volumes were used. (See also S. J. Gregg et al., *Adsorption, Surface Area and Porosity*, 2nd ed., Academic Press, 1982). In each instance, a graph of the amount adsorbed versus the relative pressure above the sample, at equilibrium, constitutes the adsorption isotherm. It is common to use relative pressures which are obtained by forming the ratio of the equilibrium pressure and the vapor pressure $P_o$ of the adsorbate at the temperature where the isotherm is measured. Sufficiently small amounts of argon were admitted in each step to generate 168 data points in the relative pressure range from 0 to 0.6. At least about 100 points are required to define the isotherm with sufficient detail.

The step (inflection) in the isotherm, indicates filling of a pore system. The size of the step indicates the amount adsorbed, whereas the position of the step in terms of $P/P_o$ reflects the size of the pores in which the adsorption takes place. Larger pores are filled at higher $P/P_o$. In order to better locate the position of the step in the isotherm, the derivative with respect to log $(P/P_o)$ is formed. The adsorption peak (stated in terms of log $(P/P_o)$) may be related to the physical pore diameter (Å) by the following formula:

$$\log(P/P_o) = \frac{K}{d - 0.38}\left(\frac{S^4}{3(L - D/2)^3} - \frac{S^{10}}{9(L - D/2)^9} - \frac{S^4}{3(D/2)^3} + \frac{S^{10}}{9(D/2)^9}\right)$$

where d=pore diameter in nanometers, K=32.17, S=0.2446, L=d+0.19, and D=0.57.

This formula is derived from the method of Horvath and Kawazoe (G. Horvath et al., *J. Chem. Eng. Japan*, 16 (6) 470(1983)). The constants required for the implementation of this formula were determined from a measured isotherm of AlPO4-5 and its known pore size. This method is particularly useful for microporous materials having pores of up to about 60 Angstroms in diameter.

The X-ray diffraction pattern for this pillared, calcined material of Example 8 is given in the following Table 15.

TABLE 15

| 2 Theta | d (A) | $I/I_o \times 100$ | |
|---|---|---|---|
| 1.7 | 52.0 | 100 | |
| 7.13 | 12.40 | 23.3 | |
| 8.08 | 10.94 | 7.3 | broad |
| 12.84 | 6.89 | 1.5 | |
| 14.38 | 6.16 | 8.4 | |
| 15.83 | 5.60 | 0.9 | |
| 19.88 | 4.47 | 2.3 | broad |
| 21.61 | 4.11 | 2.2 | |
| 22.07 | 4.0 | 3.3 | broad |
| 22.67 | 3.92 | 4.3 | broad |
| 23.67 | 3.76 | 2.7 | |
| 25.06 | 3.55 | 4.0 | |
| 26.06 | 3.42 | 12.8 | |
| 26.75 | 3.33 | 4.1 | |

EXAMPLE 9

This Example describes a preparation involving pillaring with an aqueous solution of tetramethylammomium silicate, TMA-Si, previously defined in Example 3 and formulation of the alumina bound catalyst.

The swollen product was obtained by reacting 330 g of the Example 1 wet cake (42% solids) and 2700 ml of 29% CTMA-OH for 48 hours in the steambox. The solid was isolated by filtration, washed by contacting with 0.5 l of water and air dried. The X-ray diffraction pattern of this swollen material is given in the following Table 16.

TABLE 16

| 2 Theta | d (A) | $I/I_o \times 100$ | |
|---|---|---|---|
| 1.7 | 52.0 | 100 | |
| 2.7 | 32.7 | 28.1 | |
| 5.38 | 16.43 | 10.8 | |
| 7.12 | 12.41 | 14.5 | |
| 8.10 | 10.91 | 2.9 | |
| 9.61 | 9.20 | 1.5 | broad |
| 12.77 | 6.93 | 1.0 | |
| 14.50 | 6.11 | 0.9 | |
| 19.88 | 4.47 | 6.8 | broad |
| 21.41 | 4.15 | 6.6 | |
| 21.94 | 4.05 | 4.4 | |
| 22.46 | 3.96 | 7.7 | |
| 23.05 | 3.86 | 3.3 | shoulder |
| 23.60 | 3.77 | 3.2 | shoulder |
| 24.93 | 3.57 | 4.8 | |
| 25.93 | 3.44 | 12.4 | |

TABLE 16-continued

| 2 Theta | d (A) | I/I$_o$ × 100 |
|---|---|---|
| 26.55 | 3.36 | 4.7 broad |

25 g of the above swollen material was slurried with 150 g of the TMA-Si solution and heated in a steambox for 20 hours. The solid product was filtered and air dried (yield 31 g). A small sample was calcined to verify that it was the pillaring was successful.

The remainder of the product was mixed with alumina alpha-monohydrate (Kaiser alumina) (solid ratio 65:35) and ion exchanged by contacting three times with 1M ammonium nitrate. After drying, the solid was pelletized and was calcined by a hybrid method: 3 hr in nitrogen at 450° C. followed by slow bleeding of air and full air calcination at 540° C. for 6 hours.

EXAMPLE 10

This Example describes the preparation, swelling and pillaring of the material related to that of Example 1 but with a higher content of alumina (Si/Al$_2$ ratio around 18).

A combination of 258 g of water, 6 g of 50% sodium hydroxide, 13.4 g of sodium aluminate (25% Al$_2$O$_3$, 19% Na$_2$O), 51.4 g of silica (Ultrasil), and 271 g of hexamethyleneimmine was reacted in an autoclave at 143° C. for 34 hours with stirring. The solid product was isolated by filtration and washed with water.

70 g of the above wet cake (about 20% solids) was swollen by contacting with 300 ml of 29% CTMA-OH for 43 hours at room temperature with stirring. The product was isolated by filtration, washed with water and air dried. It was then pillared (19 g) by mixing with TMA-Si (113 g) and heating in the steambox for 20 hr. Further processing, including binding with alumina, exchange and calcination was carried out as in Example 9. The X-ray diffraction pattern for this pillared, calcined material is given in the following Table 17.

TABLE 17

| 2 Theta | d (A) | I/I$_o$ × 100 |
|---|---|---|
| 1.5 | 58.9 | 100 |
| 7.13 | 12.40 | 55 |
| 8.20 | 10.78 | 19 broad |
| 12.84 | 6.89 | 5 |
| 14.41 | 6.15 | 26 |
| 15.56 | 5.69 | 5 |
| 20.04 | 4.43 | 9 |
| 21.70 | 4.10 | 9 broad shoulder |
| 22.14 | 4.01 | 12 broad |
| 22.60 | 3.93 | 19 broad |
| 23.50 | 3.79 | 13 broad |
| 25.09 | 3.55 | 11 |
| 26.04 | 3.42 | 33 |
| 26.64 | 3.35 | 21 |

EXAMPLE 11

This Example describes swelling of the material of Example 1 with dodecyltrimethylammonium chloride/hydroxide.

The swelling reagent, was prepared by contacting a 33% solution of dodecyltrimethylammonium (N,N,N-trimethyl-1-dodecanaminium) chloride with a hydroxide-for-halide exchange resin (one liter of wet resin with 1.4 milliequivalent/ml exchange capacity per 2 l of the solution). It will be referred to as 33% DOTMA-OH.

The wet cake of Example 1 (50 g, about 20% solids) was mixed with 500 ml g of DOTMA-OH and heated in the steambox for 48 hours. The solid was isolated by filtration and washed with water. The air dried product showed X-ray diffraction pattern similar to that of FIG. 2 with a very intense low angle line. The X-ray diffraction pattern for this swollen material is given in the following Table 18.

TABLE 18

| 2 Theta | d (A) | I/I$_o$ × 100 |
|---|---|---|
| 1.7 | 52.0 | 100 |
| 6.15 | 14.37 | 25 broad |
| 6.31 | 14.01 | 6 |
| 7.02 | 12.59 | 18 |
| 7.92 | 11.16 | 6 |
| 9.39 | 9.42 | 11 |
| 12.74 | 6.95 | 6 |
| 14.13 | 6.27 | 7 broad |
| 5.63 | 5.67 | 7 |
| 18.88 | 4.70 | 11 broad |
| 19.95 | 4.45 | 20 broad |
| 22.34 | 3.98 | 17 |
| 23.49 | 3.79 | 7 |
| 24.85 | 3.58 | 13 |
| 25.81 | 3.45 | 28 |
| 26.57 | 3.35 | 12 |
| 27.93 | 3.19 | 14 |

A portion of the swollen product was mixed with the TMA-silicate solution described above (Example 3) in the weight ratio 1:10, respectively. After 20 hours reaction in the steambox the solid was filtered off, air dried and contacted three times with 1M ammonium nitrate. The final product, obtained by calcination at 540° C. had a pattern essentially as described in Table 4. More particularly, the X-ray diffraction pattern for this pillared, calcined material is given in the following Table 19.

TABLE 19

| 2 Theta | d (A) | I/I$_o$ × 100 |
|---|---|---|
| 1.8 | 49.1 | 100 |
| 7.13 | 12.40 | 32 |
| 8.00 | 11.05 | 13 |
| 9.88 | 8.95 | 11 |
| 12.88 | 6.87 | 4 |
| 14.32 | 6.18 | 15 |
| 15.94 | 5.56 | 4 |
| 18.17 | 4.88 | 2 |
| 20.30 | 4.37 | 8 broad |
| 21.57 | 4.12 | 6 |
| 21.96 | 4.05 | 10 |
| 22.65 | 3.93 | 15 |
| 23.75 | 3.75 | 10 |
| 25.04 | 3.56 | 9 |
| 26.06 | 3.42 | 29 |
| 26.86 | 3.32 | 9 |
| 27.66 | 3.22 | 6 broad |

EXAMPLE 12

The Alpha values for the products from Examples 3 and 9 were measured to be 75 and 116, respectively.

The following Table 20 provides common peaks observed in the X-ray diffraction (XRD) patterns for the swollen materials of the foregoing Examples 2, 4, 6, 7, 9, and 11.

TABLE 20

| 2 Theta | d (A) | I/I$_o$ × 100 |
|---|---|---|
| 1.7 | 52.0 ± 10.0 | 100 |
| 5.3 | 16.7 ± 4.0 | 2–25 |
| 7.12 | 12.41 ± 0.25 | 6–55 |
| 8.01 | 11.04 ± 0.22 | 3–9 (Note 1) |
| 9.53 | 9.28 ± 0.19 | 2–11 (Note 1) |
| 12.79 | 6.92 ± 0.14 | 1–6 |

TABLE 20-continued

| 2 Theta | d (A) | I/I$_o$ × 100 | |
|---|---|---|---|
| 14.50 | 6.11 ± 0.24 | 1-7 | |
| 15.68 | 5.65 ± 0.11 | 1-7 | (Note 3) |
| 19.82 | 4.48 ± 0.09 | 5-22 | |
| 21.94 | 4.05 ± 0.08 | 4-7 | (Note 2) |
| 22.44 | 3.96 ± 0.08 | 8-22 | (Note 1) |
| 23.41 | 3.80 ± 0.08 | 2-9 | |
| 24.93 | 3.57 ± 0.07 | 3-19 | |
| 25.92 | 3.44 ± 0.07 | 8-59 | |
| 26.57 | 3.35 ± 0.07 | 4-16 | |

(Note 1): Peak is unresolved in the XRD pattern for Example 7.
(Note 2): Peak is unresolved in the XRD pattern for Examples 7 and 11.
(Note 3): Peak is not visible in the XRD pattern for Examples 2 and 9.

TABLE 21

| 2 Theta | d (A) | I/I$_o$ × 100 | |
|---|---|---|---|
| 1.7 | 52.0 ± 12.0 | 100 | |
| 7.14 | 12.38 ± 0.25 | 9-55 | |
| 8.08 | 10.94 ± 0.22 | 3-19 | |
| 9.82 | 9.01 ± 0.18 | 1-11 | (Note 1) |
| 12.86 | 6.88 ± 0.14 | 1-5 | |
| 14.38 | 6.16 ± 0.12 | 4-26 | |
| 15.86 | 5.59 ± 0.11 | 1-5 | |
| 20.09 | 4.42 ± 0.09 | 1-9 | |
| 21.61 | 4.11 ± 0.08 | 1-9 | |
| 22.02 | 4.04 ± 0.08 | 2-12 | |
| 22.63 | 3.93 ± 0.08 | 3-19 | |
| 23.67 | 3.76 ± 0.08 | 2-13 | |
| 25.07 | 3.55 ± 0.07 | 2-11 | |
| 26.04 | 3.42 ± 0.07 | 8-35 | |
| 26.76 | 3.33 ± 0.07 | 2-21 | |

(Note 1): Peak is unresolved in the XRD pattern for Examples 8 and 10.

The synthetic crystalline material identified below as MCM-49 is also a useful catalyst in the present invention. MCM-49 transforms to a material not readily distinguishable from calcined crystalline material MCM-22 described in U.S. Pat. No. 4,954,325. MCM-49 does not appear to contain all the components apparently present in the PSH-3 composition described in U.S. Pat. No. 4,439,409. The composition of this invention is not contaminated with ZSM-12 or ZSM-5. The calcination transformation product exhibits unusual sorption capacities and unique catalytic utility when compared to PSH-3 synthesized in accordance with U.S. Pat. No. 4,439,409. MCM-49 exhibits unique catalytic utility when compared to MCM-22 synthesized as taught in U.S. Pat. No. 954,325.

The crystalline material referred to as MCM-49 has a composition involving the molar relationship:

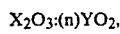

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 35, e.g. from 2 to less than about 35, usually from about 10 to less than about 35, more usually from about 15 to about 31. In the as-synthesized form, the material has a formula, on an anhydrous basis and in terms of moles of oxides per n moles of YO$_2$, as follows:

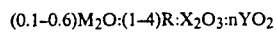

$$(0.1-0.6)M_2O:(1-4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The crystalline material MCM-49 is thermally stable and in the calcined form exhibits high surface area (greater than 400 m$^2$/gm) and unusually large sorption capacity when compared to previously described materials such as calcined PSH-3 and SSZ-25 having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-49 material appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table 21 below:

TABLE 21

| Interplanar d-Spacing (A) | Relative Intensity, I/Io × 100 |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason, the precise intensity and position of the 13.15±0.26 Angstroms peak are difficult to determine within the stated range.

In its calcined form, the crystalline MCM-49 material of the invention transforms to a single crystal phase with little or no detectable impurity crystal phases having an X-ray diffraction pattern which is not readily distinguished from that of MCM-22, but distinguishable from the patterns of other known crystalline materials. The X-ray diffraction pattern of the calcined form of MCM-49 includes the lines listed in Table 22 below:

TABLE 22

| Interplanar d-Spacing (A) | Relative Intensity, I/Io × 100 |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |

TABLE 22-continued

| Interplanar d-Spacing (A) | Relative Intensity, I/Io × 100 |
|---|---|
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60-100), s=strong (40-60), m=medium (20-40) and w=weak (0-20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g. MCM-22 and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

The present as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and ~6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. Unfortunately, the ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak. FIG. 1 shows the same segment of the diffraction patterns of precursor MCM-22, calcined MCM-22, and MCM-49; the position of the ~6.6-6.3 Angstroms peak is indicated in each segment by an asterisk. Because the 6.4 Angstroms peak is unobscured in MCM-49, it was chosen as a better means of distinguishing MCM-49 from the calcined forms of MCM-22 and PSH-3 rather than the much stronger ~12.8 Angstroms peak.

The crystalline MCM-49 material may be subjected to treatment to remove part or all of any organic constituent prior to its use as a catalyst in the present invention. The crystalline MCM-49 material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g. aluminum, is in the structure, impregnated therein or intimately physically admixed therewith. Such component can be impregnated in or on to it such as, for example, by, in the case of platinum, treating the silicate with a solution containing a platinum metal- containing ion. Thus, suitable platinum compounds for this purpose include chloroplatinic acid, platinous chloride and various compounds containing the platinum amine complex.

The crystalline MCM-49 material can be transformed to another form by thermal treatment. This thermal treatment is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of isoparaffin-olefin alkylation.

The crystalline material of this invention, when employed either as an adsorbent or as a catalyst in the process of the present invention should be dehydrated, at least partially. This can be done by heating to a temperature in the range of 200° C. to about 370° C. in an atmosphere such as air, nitrogen, etc. and at atmospheric, subatmospheric or superatmospheric pressures for between 30 minutes and 48 hours. Dehydration can also be performed at room temperature merely by placing the MCM-49 in a vacuum, but a longer time is required to obtain a sufficient amount of dehydration.

The present crystalline material can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, the reaction mixture having a composition, in terms of mole ratios of oxides, within the following ranges:

| Reactants | Useful | Preferred |
|---|---|---|
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one x component is present, at least one must be present such that the $YO_2/X_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum oxide has been added to the reaction mixture as a source of X, the $YO_2/Al_2O_3$ ratio must be less than about 35.

In the present method for synthesizing MCM-49, the source of $YO_2$ must be comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-49 formation from the above mixture. Preferably, therefore, the $YO_2$, e.g. silica, source contains at least about 30 wt. % solid $YO_2$, e.g. silica, and more preferably at least about 40 wt. % solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

Crystallization of the crystalline MCM-49 material can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of the new crystals may be facilitated by the presence of at least 0.01 percent, preferably 0.10 percent and still more preferably 1 percent, seed crystals (based on total weight) of crystalline product. Useful seed crystals include MCM-22 and/or MCM-49.

The MCM-49 crystals can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

Because of the severe conditions of temperature and pressure employed in the present process, the crystalline MCM-49 is preferably composited with another material resistant to these process conditions. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with MCM-49 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-49 also include inorganic oxides, notably alumina.

In addition to the foregoing materials, MCM-49 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the synthesis and characterization of MCM-49, the following examples are presented. In the examples, whenever sorption data are set forth for comparison of sorptive capacities for water, cyclohexane and/or n-hexane, they were Equilibrium Adsorption values determined as follows:

A weighed sample of the calcined adsorbant was contacted with the desired pure adsorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. The MCM-49 material of this invention always exhibits Equilibrium Adsorption values of greater than about 10 wt. % for water vapor, greater than about 4.3 wt. %, usually greater than about 7 wt. % for cyclohexane vapor and greater than about 10 wt. % for n-hexane vapor. These vapor sorption capacities are a notable distinguishing feature of the present crystalline material.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 13

A 1 part quantity of $Al_2(SO_4)_3 \cdot xH_2O$ was dissolved in a solution containing 1.83 parts of 50% NaOH solution and 13 parts of $H_2O$. To this were added 1.78 parts of hexamethyleneimine (HMI) followed by 6.6 parts of amorphous silica precursor (46% solids). The mixture was thoroughly mixed until uniform.

The reaction mixture had the following composition in mole ratios:

| | | |
|---|---|---|
| $SiO_2Al_2O_3$ | = | 30 |
| $OH^-/SiO_2$ | = | 0.25 |
| $Na/SiO_2$ | = | 0.43 |
| $HMI/SiO_2$ | = | 0.35 |
| $H_2O/SiO_2$ | = | 19.4 |

Figure 6:
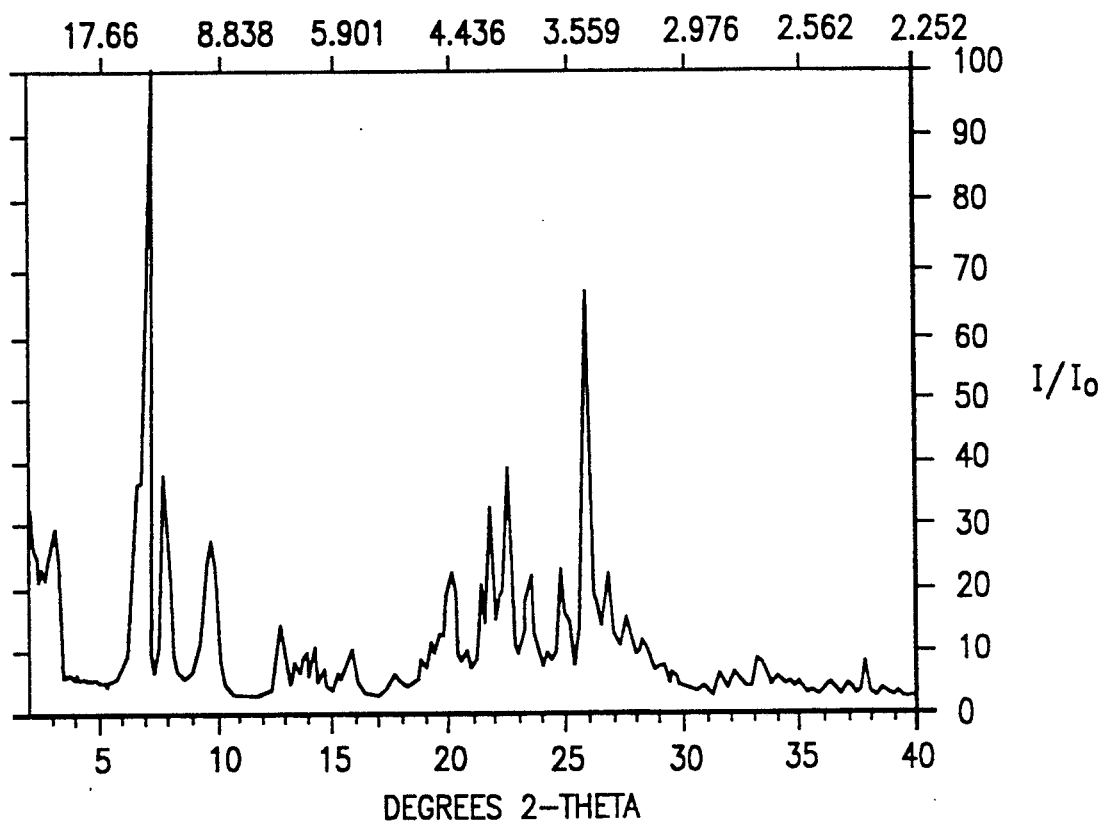
FIG. 6 is an X-ray diffraction pattern of the assynthesized crystalline material product of Example 13.

The mixture was crystallized in a stirred reactor at 150° C. for 4 days. The crystals were filtered, washed with water and dried at 120° C. A portion of the product was submitted for X-ray analysis and identified as the new crystalline material MCM-49. The material exhibited the X-ray powder diffraction pattern as shown in Table 23 and FIG. 6.

The chemical composition of the product was, in wt. %:

| | |
|---|---|
| N | 1.81 |
| Na | 0.38 |
| $Al_2O_3$ | 7.1 |
| $SiO_2$ | 72.8 |
| Ash | 79.2 |

The $SiO_2/Al_2O_3$ molar ratio of this product was 17.4.

The sorption capacities, after calcining for 6 hours at 538° C. were, in wt. %:

| | |
|---|---|
| Cyclohexane, 40 Torr | 4.4 |
| n-Hexane, 40 Torr | 12.8 |
| $H_2O$, 12 Torr | 11.1 |

A portion of the sample was calcined in air for 16 hours at 538° C. This material exhibited the X-ray diffraction pattern shown in Table 24.

TABLE 23

| Degrees 2-Theta | Interplanar d-spacing (A) | $I/I_o$ |
|---|---|---|
| 3.2 | 27.5 | 11 |
| 6.75 | 13.09 | 36 sh |
| 7.08 | 12.49 | 100 |
| 7.88 | 11.23 | 40 |
| 9.81 | 9.02 | 24 |
| 12.79 | 6.92 | 13 |
| 13.42 | 6.60 | 5* |
| 13.87 | 6.38 | 6 |
| 14.24 | 6.22 | 7 |
| 14.64 | 6.05 | 4 |
| 15.24 | 5.81 | 2 |
| 15.81 | 5.61 | 8 |
| 17.72 | 5.01 | 2 |
| 18.91 | 4.69 | 4 |
| 19.27 | 4.61 | 5 |
| 20.09 | 4.42 | 19 |
| 20.83 | 4.26 | 6 |
| 21.48 | 4.14 | 15 |
| 21.78 | 4.08 | 29 |
| 22.22 | 4.00 | 12 |
| 22.59 | 3.94 | 36 |
| 23.56 | 3.78 | 19 |
| 24.87 | 3.58 | 21 |
| 25.10 | 3.55 | 6 |
| 25.89 | 3.44 | 80 |
| 26.32 | 3.39 | 7 |
| 26.81 | 3.33 | 17 |
| 27.57 | 3.24 | 11 |
| 28.36 | 3.15 | 7 |
| 29.03 | 3.08 | 3 |
| 29.50 | 3.03 | 2 |
| 31.47 | 2.842 | 3 |
| 32.16 | 2.784 | 3 |
| 33.26 | 2.694 | 6 |
| 34.08 | 2.631 | 2 |
| 34.83 | 2.576 | 1 |
| 36.25 | 2.478 | 2 |
| 36.96 | 2.432 | 2 |
| 37.72 | 2.385 | 7 | sh = Shoulder
* = Impurity peak

TABLE 24

| Degrees 2-Theta | Interplanar d-spacing (A) | $I/I_o$ |
|---|---|---|
| 3.4 | 26.0 | 6 |
| 6.96 | 12.69 | 45 sh |
| 7.15 | 12.37 | 100 |
| 7.97 | 11.09 | 58 |
| 9.97 | 8.87 | 49 |
| 12.88 | 6.88 | 10 |
| 13.50 | 6.56 | 3* |
| 14.34 | 6.18 | 26 |
| 14.76 | 6.00 | 8 |

TABLE 24-continued

| Degrees 2-Theta | Interplanar d-spacing (A) | I/I$_o$ |
|---|---|---|
| 15.30 | 5.79 | 1 |
| 15.96 | 5.55 | 13 |
| 17.84 | 4.97 | 1 |
| 19.03 | 4.66 | 3 |
| 19.34 | 4.59 | 2 |
| 19.67 | 4.51 | 2* |
| 20.26 | 4.38 | 10 |
| 21.18 | 4.20 | 3 |
| 21.59 | 4.12 | 10 |
| 21.88 | 4.06 | 17 |
| 22.40 | 3.97 | 8 |
| 22.72 | 3.91 | 28 |
| 23.74 | 3.75 | 16 |
| 24.73 | 3.60 | 3 |
| 24.98 | 3.57 | 10 |
| 25.23 | 3.53 | 5 |
| 26.00 | 3.43 | 57 |
| 26.98 | 3.30 | 12 |
| 27.81 | 3.21 | 12 |
| 28.64 | 3.12 | 7 |
| 29.14 | 3.06 | 2 |
| 29.69 | 3.01 | 2 |
| 31.62 | 2.830 | 3 |
| 32.28 | 2.773 | 3 |
| 33.38 | 2.685 | 6 |
| 34.43 | 2.605 | 2 |
| 34.98 | 2.565 | 2 |
| 36.39 | 2.469 | 1 |
| 37.09 | 2.424 | 2 |
| 37.86 | 2.377 | 4 | sh = Shoulder
* = Impurity peak

The calcined portion of the product of Example 13 was ammonium exchanged and calcined at 538° C. in air for 16 hours to provide the hydrogen form transformation product of the crystalline MCM-49. The Alpha Test proved this material to have an Alpha Value of 291.

EXAMPLE 15

A 1.45 part quantity of sodium aluminate was added to a solution containing 1 part of 50% NaOH solution and 53.1 parts H$_2$O. A 5.4 part quantity of HMI was added, followed by 10.3 parts of Ultrasil, a precipitated spray-dried silica (about 90% SiO$_2$). The reaction mixture was thoroughly mixed and transferred to a stainless steel autoclave equipped with a stirrer.

The reaction mixture had the following composition in mole ratios:

| | | |
|---|---|---|
| SiO$_2$/Al$_2$O$_3$ | = | 25 |
| OH$^-$/SiO$_2$ | = | 0.19 |
| Na/SiO$_2$ | = | 0.19 |
| HMI/SiO$_2$ | = | 0.35 |
| H$_2$O/SiO$_2$ | = | 19.3 |

Figure 7:
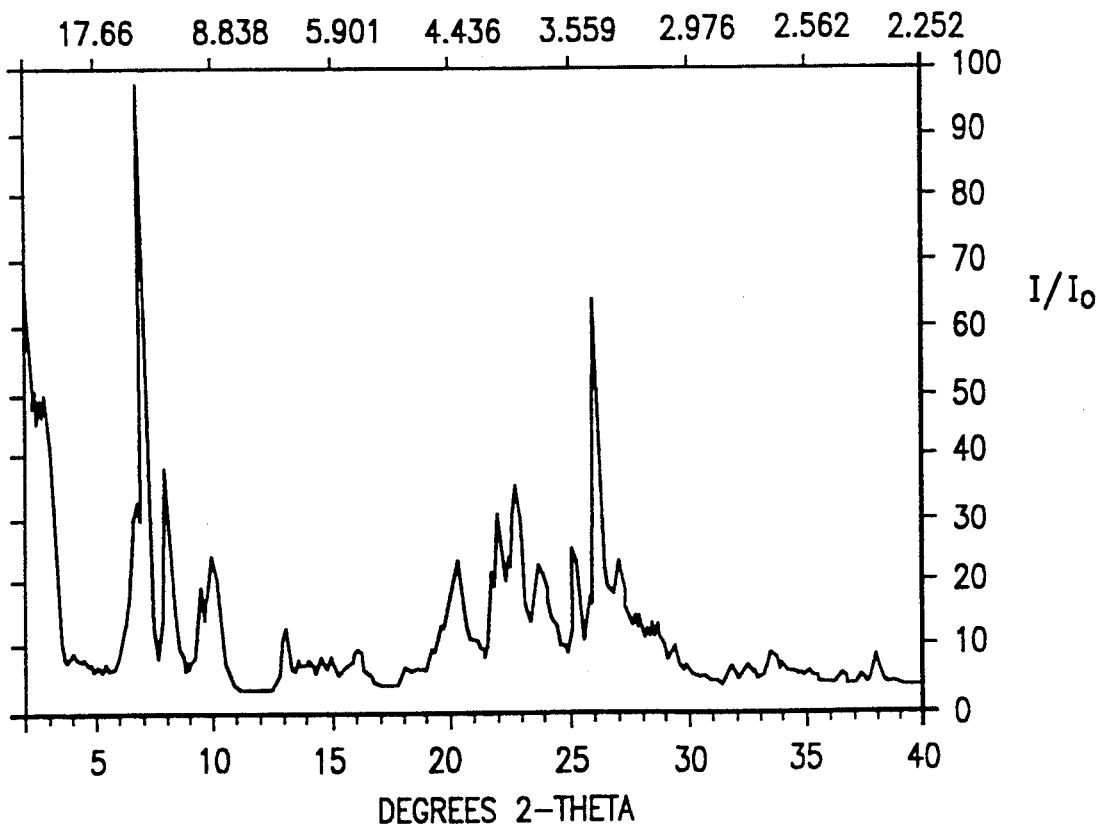
FIG. 7 is an X-ray diffraction pattern of the assynthesized crystalline material product of Example 15.

The mixture was crystallized with stirring at 150° C. for 8 days. The product was identified as poorly crystalline MCM-49 and had the X-ray pattern which appears in Table 25 and FIG. 7.

The chemical composition of the product was, in wt. %:

| | |
|---|---|
| N | 2.29 |
| Na | 0.19 |
| Al$_2$O$_3$ | 6.3 |
| SiO$_2$ | 71.0 |
| Ash | 77.9 |

The silica/alumina mole ratio of the product was 19.2.

The sorption capacities, after calcining for 16 hours at 538° C. were, in wt. %:

| | |
|---|---|
| Cyclohexane, 40 Torr | 9.9 |
| n-Hexane, 40 Torr | 14.6 |
| H$_2$O, 12 Torr | 15.1 |

A portion of the sample was calcined in air for 16 hours at 538° C. This material exhibited the X-ray diffraction pattern shown in Table 26.

TABLE 25

| Degrees 2-Theta | Interplanar d-spacing (A) | I/I$_o$ |
|---|---|---|
| 3.0 | 29.3 | 8 |
| 3.9 | 22.8 | 2+ |
| 6.66 | 13.27 | 34 |
| 7.10 | 12.45 | 100 |
| 7.91 | 11.18 | 39 |
| 9.24 | 9.57 | 16* |
| 9.79 | 9.04 | 23 |
| 12.79 | 6.92 | 11 |
| 13.60 | 6.51 | 5 |
| 14.28 | 6.20 | 5 |
| 14.68 | 6.03 | 5 |
| 15.33 | 5.78 | 2 |
| 15.83 | 5.60 | 7 |
| 17.80 | 4.98 | 2 |
| 18.94 | 4.68 | 3 |
| 19.32 | 4.59 | 8 |
| 20.09 | 4.42 | 21 |
| 21.51 | 4.13 | 17 |
| 21.82 | 4.07 | 27 |
| 22.17 | 4.01 | 13 |
| 22.58 | 3.94 | 33 |
| 23.50 | 3.79 | 19 |
| 24.09 | 3.69 | 8* |
| 24.96 | 3.57 | 23 |
| 25.55 | 3.49 | 11* |
| 25.93 | 3.44 | 73 |
| 26.82 | 3.32 | 20 |
| 27.54 | 3.24 | 9 |
| 28.32 | 3.15 | 9** |
| 29.07 | 3.07 | 5** |
| 31.50 | 2.840 | 3 |
| 32.15 | 2.784 | 3 |
| 33.31 | 2.690 | 6 |
| 34.48 | 2.601 | 2 |
| 36.26 | 2.478 | 2 |
| 37.03 | 2.428 | 2 |
| 37.75 | 2.383 | 6 |

+ = Non-crystallographic MCM-49 peak
* = Impurity peak
** = May contain impurity peak

TABLE 26

| Degrees 2-Theta | Interplanar d-spacing (A) | I/I$_o$ |
|---|---|---|
| 3.9 | 22.8 | 6+ |
| 6.88 | 12.84 | 46 sh |
| 7.11 | 12.43 | 100 |
| 7.97 | 11.10 | 57 |
| 9.35 | 9.46 | 25* |
| 9.94 | 8.90 | 48 |
| 12.53 | 7.07 | 4* |
| 12.82 | 6.90 | 13 |
| 13.41 | 6.60 | 3* |
| 14.30 | 6.19 | 36 |
| 14.73 | 6.01 | 6 |
| 15.93 | 5.56 | 10 |
| 17.90 | 4.96 | 2 |
| 18.98 | 4.68 | 3 |
| 19.34 | 4.59 | 3 |
| 20.18 | 4.40 | 11 |
| 21.56 | 4.12 | 11 |
| 21.86 | 4.07 | 18 |
| 22.34 | 3.98 | 10 |

TABLE 26-continued

| Degrees 2-Theta | Interplanar d-spacing (A) | I/I$_o$ |
|---|---|---|
| 22.67 | 3.92 | 30 |
| 23.68 | 3.76 | 17 |
| 24.94 | 3.57 | 15 |
| 25.20 | 3.53 | 6* |
| 25.97 | 3.43 | 60 |
| 25.93 | 3.31 | 13 |
| 27.79 | 3.21 | 11 |
| 28.56 | 3.13 | 8** |
| 29.10 | 3.07 | 3** |
| 29.60 | 3.02 | 1 |
| 31.58 | 2.83 | 3 |
| 32.24 | 2.776 | 3 |
| 33.34 | 2.688 | 7 |
| 34.59 | 2.593 | 3 |
| 36.33 | 2.473 | 1 |
| 37.05 | 2.426 | 2 |
| 37.79 | 2.380 | 4 | sh = Shoulder
+ = Non-crystallographic MCM-49 peak
* = Impurity peak
** = May contain impurity peak

EXAMPLE 16

The calcined portion of the product of Example 15 was ammonium exchanged and calcined at 538° C. in air for 16 hours to provide the hydrogen form transformation product of the crystalline MCM-49. The Alpha Test proved this material to have an Alpha Value of 286.

EXAMPLE 17

A 10.5 part quantity of gallium oxide was added to a solution containing 1.0 part sodium aluminate, 3.05 parts 50% NaOH solution and 280 parts H$_2$O. A 25.6 part quantity of HMI was added followed by 56.6 parts of Ultrasil and 1.7 parts of MCM-22 seeds. The slurry was thoroughly mixed.

The composition of the reaction mixture in mole ratios:

| | | |
|---|---|---|
| SiO$_2$/Al$_2$O$_3$ | = | 138 |
| SiO$_2$/Ga$_2$O$_3$ | = | 17.9 |
| OH$^-$/SiO$_2$ | = | 0.057 |
| Na/SiO$_2$ | = | 0.057 |
| HMI/SiO$_2$ | = | 0.30 |
| H$_2$O/SiO$_2$ | = | 18.4 |

Figure 8:
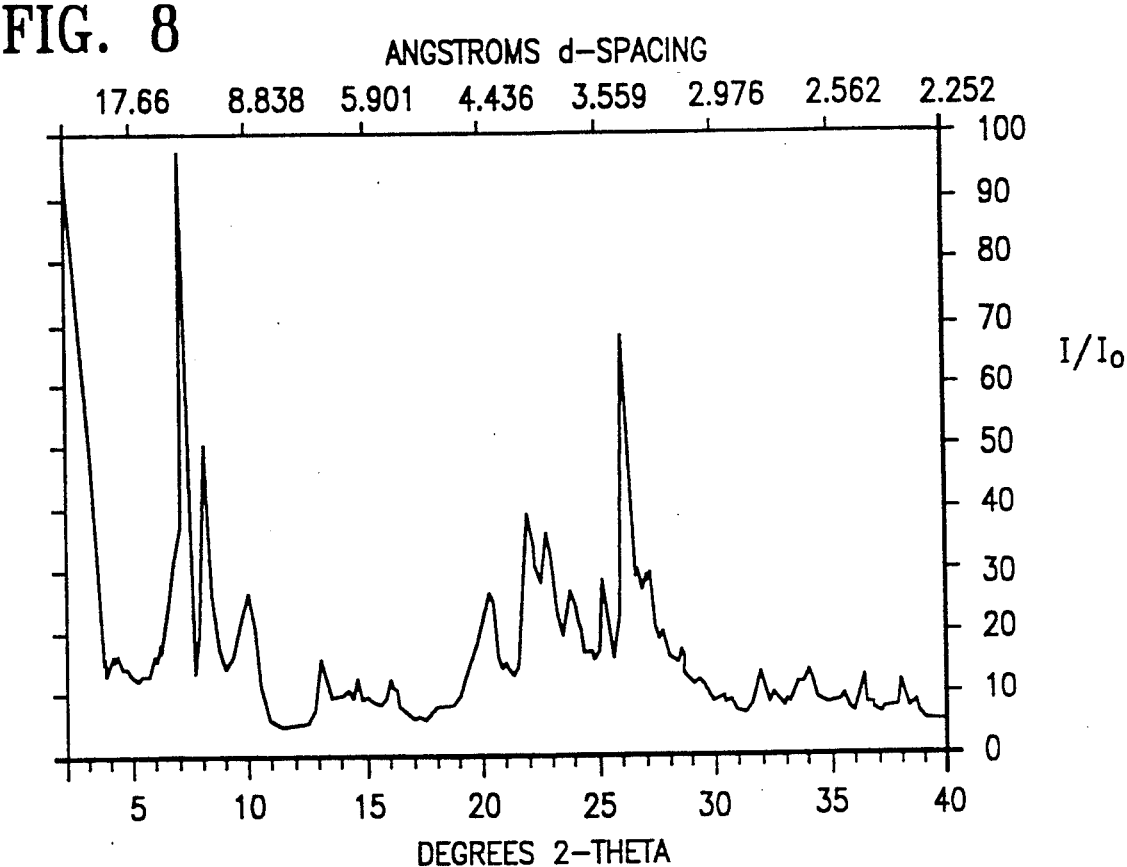
FIG. 8 is an X-ray diffraction pattern of the assynthesized crystalline material product of Example 17.

The mixture was crystallized with stirring at 150° C. for 10 days. The product was identified as poorly crystalline MCM-49 and had the X-ray pattern which appears in Table 27 and FIG. 8.

The chemical composition of the product was, in wt. %:

| | |
|---|---|
| N | 1.89 |
| Na | 0.40 |
| Ga | 8.5 |
| Al$_2$O$_3$ | 0.81 |
| SiO$_2$ | 65.6 |
| Ash | 79.3 | with silica/alumina and silica/gallia molar ratios for the product of:

| | |
|---|---|
| SiO$_2$/Al$_2$O$_3$ | 138 |
| SiO$_2$/Ga$_2$O$_3$ | 17.9 |

The sorption capacities, after calcining for 3 hours at 538° C. were, in wt. %:

| | |
|---|---|
| Cyclohexane, 40 Torr | 13.3 |
| n-Hexane, 40 Torr | 11.3 |
| H$_2$O, 12 Torr | 12.3 |

A portion of the sample was calcined in air for 16 hours at 538° C. This material exhibited the X-ray diffraction pattern shown in Table 28.

TABLE 27

| Degrees 2-Theta | Interplanar d-spacing (A) | I/I$_o$ |
|---|---|---|
| 3.9 | 22.8 | 6+ |
| 6.66 | 13.27 | 30 sh |
| 7.08 | 12.48 | 100 |
| 7.92 | 11.17 | 43 |
| 9.27 | 9.54 | 8* |
| 9.74 | 9.08 | 20 |
| 12.78 | 6.93 | 12 |
| 13.75 | 6.44 | 6 |
| 14.28 | 6.20 | 5 |
| 14.62 | 6.06 | 3 |
| 15.78 | 5.62 | 8 |
| 17.99 | 4.93 | 3 |
| 18.92 | 4.69 | 6 |
| 20.10 | 4.42 | 24 |
| 20.86 | 4.26 | 9 |
| 21.47 | 4.14 | 10 |
| 21.73 | 4.09 | 26 |
| 22.57 | 3.94 | 29 |
| 23.53 | 3.78 | 22 |
| 24.92 | 3.57 | 24 |
| 25.91 | 3.44 | 82 |
| 26.80 | 3.33 | 19 |
| 27.43 | 3.25 | 14 |
| 28.31 | 3.15 | 10 |
| 29.04 | 3.07 | 5 |
| 31.59 | 2.832 | 8 |
| 32.17 | 2.783 | 3 |
| 33.25 | 2.694 | 6 |
| 33.70 | 2.659 | 8* |
| 35.12 | 2.555 | 4* |
| 35.96 | 2.497 | 11* |
| 36.29 | 2.476 | 4 |
| 37.73 | 2.384 | 7 | sh = Shoulder
+ = Non-crystallographic MCM-49 peak
* = Impurity peak

TABLE 28

| Degrees 2-Theta | Interplanar d-spacing (A) | I/I$_o$ |
|---|---|---|
| 3.9 | 22.8 | 11+ |
| 6.89 | 12.83 | 40 sh |
| 7.11 | 12.43 | 100 |
| 7.96 | 11.11 | 55 |
| 9.40 | 9.41 | 10* |
| 9.94 | 8.90 | 47 |
| 12.81 | 6.91 | 10 |
| 14.31 | 6.19 | 32 |
| 14.74 | 6.01 | 4 |
| 15.94 | 5.56 | 12 |
| 17.89 | 4.96 | <1 |
| 19.00 | 4.67 | 3 |
| 19.39 | 4.58 | 3 |
| 20.22 | 4.39 | 9 |
| 21.56 | 4.12 | 9 |
| 21.86 | 4.07 | 17 |
| 22.70 | 3.92 | 29 |
| 23.70 | 3.75 | 16 |
| 24.99 | 3.56 | 14 |

TABLE 28-continued

| Degrees 2-Theta | Interplanar d-spacing (A) | $I/I_o$ |
|---|---|---|
| 26.01 | 3.43 | 57 |
| 26.96 | 3.31 | 12 |
| 27.84 | 3.20 | 10 |
| 28.60 | 3.12 | 5 |
| 29.10 | 3.07 | 3 |
| 31.63 | 2.829 | 6 |
| 32.28 | 2.773 | 3 |
| 33.39 | 2.684 | 7 |
| 33.72 | 2.658 | 9* |
| 35.07 | 2.559 | 4* |
| 35.94 | 2.499 | 4* |
| 35.40 | 2.468 | 1 |
| 37.13 | 2.422 | 2 |
| 37.88 | 2.375 | 3 | sh = Shoulder
+ = Non-crystallographic MCM-49 peak
* = Impurity peak

EXAMPLE 18

The calcined portion of the product of Example 17 was ammonium exchanged and calcined at 538° C. in air for 16 hours to provide the hydrogen form transformation product of the crystalline MCM-49. The Alpha Test proved this material to have an Alpha Value of 64.

EXAMPLE 19

A solution containing 1 part of $Al_2(SO_4)_3 \cdot xH_2O$, 1.31 parts of 50% NaOH solution and 14.0 parts of $H_2O$ was prepared. To this were added 2.8 parts of Ultrasil precipitated silica followed by 1.48 parts of HMI. The reaction mixture was thoroughly mixed. The composition of the reaction mixture in mole ratios was:

| | | |
|---|---|---|
| $SiO_2/Al_2O_3$ | = | 25.5 |
| $OH^-/SiO_2$ | = | 0.15 |
| $Na/SiO_2$ | = | 0.39 |
| $HMI/SiO_2$ | = | 0.35 |
| $H_2O/SiO_2$ | = | 19.4 |

Figure 9:
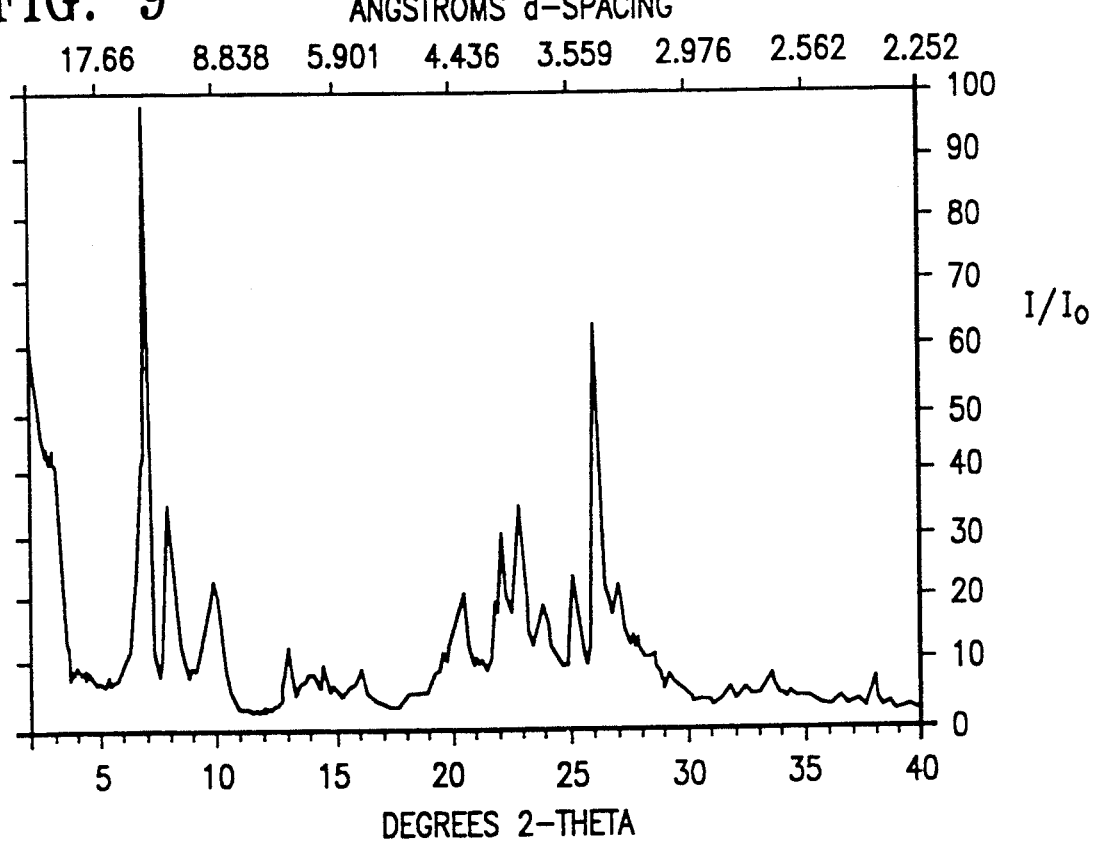
FIG. 9 is an X-ray diffraction pattern of the assynthesized crystalline material product of Example 19.

The mixture was crystallized for 5 days at 143° C. The product was washed, dried at 120° C. and identified by X-ray analysis as MCM-49. It exhibited an X-ray pattern as shown in Table 29 and FIG. 9.

The sorption capacities, after calcining for 16 hours at 538° C. were, in wt. %:

| | |
|---|---|
| Cyclohexane, 40 Torr | 8.8 |
| n-Hexane, 40 Torr | 15.9 |
| $H_2O$, 12 Torr | 13.6 |

The chemical composition of the product was, in wt. %:

| | |
|---|---|
| N | 1.83 |
| Na | 0.27 |
| $Al_2O_3$ | 6.8 |
| $SiO_2$ | 73.8 |
| Ash | 80.5 |

The silica/alumina mole ratio of the product was 18.4.
The surface area of this material was measured to be 459 m²/g.
A portion of the sample was calcined in air for 16 hours at 538° C. This material exhibited the X-ray diffraction pattern shown in Table 30.

TABLE 29

| Degrees 2-Theta | Interplanar d-spacing (A) | $I/I_o$ |
|---|---|---|
| 3.1 | 28.5 | 17 |
| 4.0 | 22.2 | 3+ |
| 6.73 | 13.14 | 43 sh |
| 7.08 | 12.48 | 100 |
| 7.92 | 11.16 | 42 |
| 9.69 | 9.13 | 23 |
| 12.80 | 6.91 | 13 |
| 13.76 | 6.44 | 7 |
| 14.27 | 6.20 | 6 |
| 14.65 | 6.05 | 3 |
| 15.85 | 5.59 | 7 |
| 17.82 | 4.98 | 2 |
| 18.92 | 4.69 | 3 |
| 19.32 | 4.59 | 8 |
| 20.13 | 4.41 | 20 |
| 21.48 | 4.14 | 12 |
| 21.82 | 4.07 | 31 |
| 22.56 | 3.94 | 36 |
| 23.59 | 3.77 | 18 |
| 24.91 | 3.57 | 22 |
| 25.91 | 3.44 | 79 |
| 26.74 | 3.33 | 20 |
| 27.61 | 3.23 | 7 |
| 28.25 | 3.16 | 8 |
| 29.14 | 3.06 | 3 |
| 31.48 | 2.842 | 3 |
| 31.16 | 2.783 | 3 |
| 33.26 | 2.694 | 6 |
| 33.85 | 2.648 | 3 sh |
| 34.72 | 2.584 | 2 |
| 36.26 | 2.478 | 2 |
| 37.00 | 2.429 | 2 |
| 37.73 | 2.384 | 7 | sh = Shoulder
+ = Non-crystallographic MCM-49 peak

TABLE 30

| Degrees 2-Theta | Interplanar d-spacing (A) | $I/I_o$ |
|---|---|---|
| 3.9 | 22.8 | 6+ |
| 6.91 | 12.79 | 38 sh |
| 7.12 | 12.42 | 100 |
| 7.96 | 11.10 | 53 |
| 9.94 | 8.90 | 39 |
| 12.84 | 6.90 | 11 |
| 14.30 | 6.19 | 39 |
| 14.71 | 6.02 | 10 |
| 15.92 | 5.57 | 12 |
| 18.00 | 4.93 | 1 |
| 18.98 | 4.67 | 3 |
| 19.34 | 4.59 | 3 |
| 20.17 | 4.40 | 10 |
| 21.55 | 4.12 | 10 |
| 21.86 | 4.07 | 17 |
| 22.67 | 3.92 | 27 |
| 23.69 | 3.75 | 15 |
| 24.96 | 3.57 | 13 |
| 25.98 | 3.43 | 61 |
| 26.93 | 3.31 | 13 |
| 27.80 | 3.21 | 9 |
| 28.58 | 3.12 | 6 |
| 29.11 | 3.07 | 2 |
| 29.63 | 3.02 | 1 |
| 31.57 | 2.834 | 3 |
| 32.23 | 2.777 | 3 |
| 33.35 | 2.687 | 6 |
| 34.60 | 2.593 | 3 |
| 36.34 | 2.472 | 1 |
| 37.06 | 2.426 | 1 |
| 37.83 | 2.378 | 5 | sh = Shoulder
+ = Non-crystallographic MCM-49 peak

EXAMPLE 20

A 2.24 part quantity of 45% sodium aluminate was added to a solution containing 1.0 part of 50% NaOH solution and 43.0 parts H$_2$O in an autoclave. An 8.57 part quantity of Ultrasil precipitated silica was added with agitation, followed by 4.51 parts of HMI.

The reaction mixture had the following composition, in mole ratios:

| | |
|---|---|
| SiO$_2$/Al$_2$O$_3$ | = 23 |
| OH$^-$/SiO$_2$ | = 0.21 |
| Na/SiO$_2$ | = 0.21 |
| HMI/SiO$_2$ | = 0.35 |
| H$_2$O/SiO$_2$ | = 19.3 |

Figure 10:
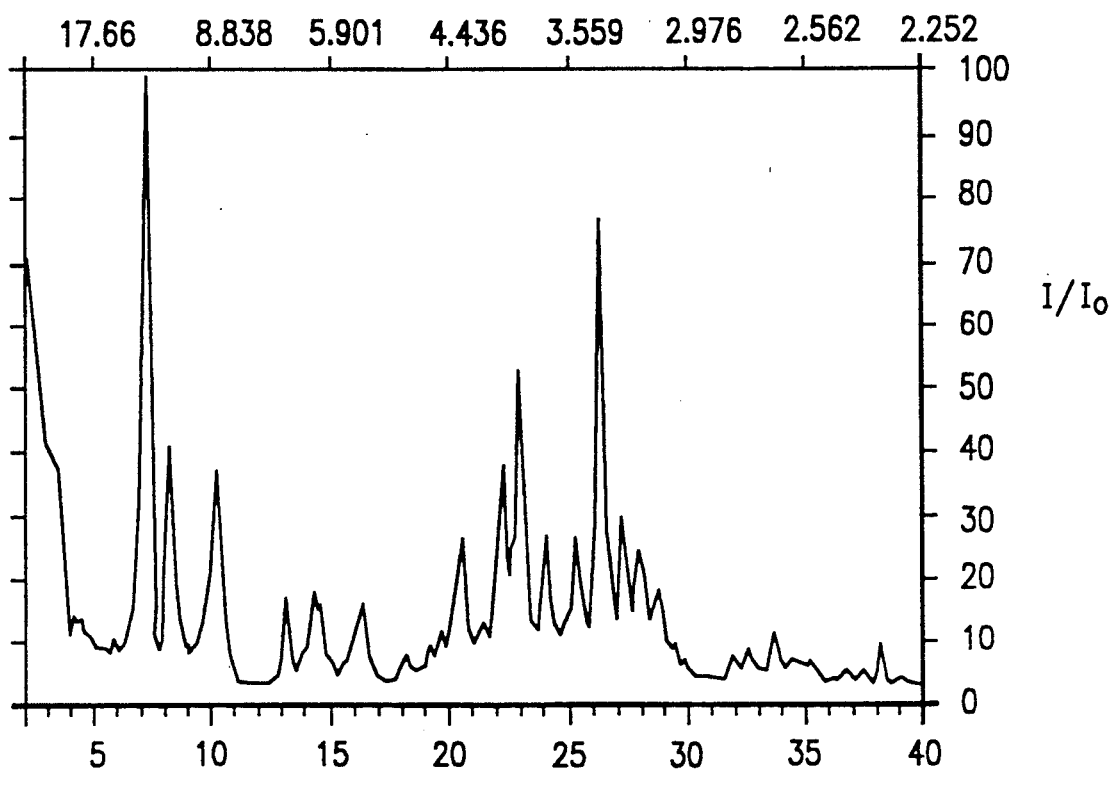
FIG. 10 is an X-ray diffraction pattern of the assynthesized crystalline material product of Example 20.

The mixture was crystallized at 150° C. stirring. The product was identified as MCM-49 and had the X-ray pattern which appears in Table 31 and FIG. 10.

The chemical composition of the product was, in wt. %:

| | |
|---|---|
| N | 1.70 |
| Na | 0.70 |
| Al$_2$O$_3$ | 7.3 |
| SiO$_2$ | 74.5 |
| Ash | 84.2 |

The silica/alumina mole ratio of the product was 17.3.

The sorption capacities, after calcining at 538° C. for 9 hours were, in wt. %:

| | |
|---|---|
| Cyclohexane, 40 Torr | 10.0 |
| n-Hexane, 40 Torr | 13.1 |
| H$_2$O, 12 Torr | 15.4 |

A portion of the sample was calcined in air for 3 hours at 538° C. This material exhibited the X-ray diffraction pattern shown in Table 32.

TABLE 31

| Degrees 2-Theta | Interplanar d-spacing (A) | I/I$_o$ |
|---|---|---|
| 3.1 | 28.5 | 18 |
| 3.9 | 22.8 | 7+ |
| 6.81 | 12.99 | 61 sh |
| 7.04 | 12.55 | 97 |
| 7.89 | 11.21 | 41 |
| 9.80 | 9.03 | 40 |
| 12.76 | 6.94 | 17 |
| 13.42 | 6.60 | 4* |
| 13.92 | 6.36 | 17 |
| 14.22 | 6.23 | 11 |
| 14.63 | 6.05 | 2 |
| 15.81 | 5.61 | 15 |
| 17.71 | 5.01 | 4 |
| 18.86 | 4.71 | 4 |
| 19.23 | 4.62 | 6 |
| 20.09 | 4.42 | 27 |
| 20.93 | 4.24 | 8 |
| 21.44 | 4.14 | 17 |
| 21.74 | 4.09 | 37 |
| 22.16 | 4.01 | 17 |
| 22.56 | 3.94 | 58 |
| 23.53 | 3.78 | 26 |
| 24.83 | 3.59 | 22 |
| 25.08 | 3.55 | 10 |
| 25.86 | 3.45 | 100 |
| 26.80 | 3.33 | 28 |
| 27.53 | 3.24 | 21 |
| 28.33 | 3.15 | 15 |
| 28.98 | 3.08 | 4 |
| 29.47 | 3.03 | 2 |

TABLE 31-continued

| Degrees 2-Theta | Interplanar d-spacing (A) | I/I$_o$ |
|---|---|---|
| 31.46 | 2.843 | 4 |
| 32.08 | 2.790 | 6 |
| 33.19 | 2.699 | 9 |
| 34.05 | 2.633 | 5 |
| 34.77 | 2.580 | 4 |
| 36.21 | 2.481 | 2 |
| 36.90 | 2.436 | 3 |
| 37.68 | 2.387 | 8 | sh = Shoulder
+ = Non-crystallographic MCM-49 peak
* = Impurity peak

TABLE 32

| Degrees 2-Theta | Interplanar d-spacing (A) | I/I$_o$ |
|---|---|---|
| 3.2 | 28.0 | 9 |
| 3.9 | 22.8 | 7+ |
| 6.90 | 12.81 | 48 sh |
| 7.13 | 12.39 | 100 |
| 7.98 | 11.08 | 46 |
| 9.95 | 8.89 | 53 |
| 12.87 | 6.88 | 10 |
| 14.32 | 6.18 | 36 |
| 14.74 | 6.01 | 11 |
| 15.94 | 5.56 | 17 |
| 17.87 | 4.96 | 2 |
| 19.00 | 4.67 | 5 |
| 19.35 | 4.59 | 3 |
| 20.24 | 4.39 | 14 |
| 21.06 | 4.22 | 5 |
| 21.56 | 4.12 | 15 |
| 21.87 | 4.06 | 25 |
| 22.32 | 3.98 | 12 |
| 22.69 | 3.92 | 41 |
| 23.69 | 3.76 | 23 |
| 24.95 | 3.57 | 19 |
| 25.22 | 3.53 | 4 |
| 25.99 | 3.43 | 90 |
| 26.94 | 3.31 | 20 |
| 27.73 | 3.22 | 17 |
| 28.55 | 3.13 | 11 |
| 29.11 | 3.07 | 3 |
| 29.63 | 3.01 | 2 |
| 31.59 | 2.833 | 6 |
| 32.23 | 2.777 | 4 |
| 33.34 | 2.687 | 9 |
| 34.35 | 2.611 | 4 |
| 34.92 | 2.570 | 3 |
| 36.35 | 2.471 | 2 |
| 37.07 | 2.425 | 2 |
| 37.82 | 2.379 | 6 | sh = Shoulder
+ = Non-crystallographic MCM-49 peak

EXAMPLE 21

The calcined portion of the product of Example 20 was ammonium exchanged and calcined at 538° C. in air for 3 hours to provide the hydrogen form transformation product of the crystalline MCM-49. The Alpha Test proved this material to have an Alpha Value of 308.

EXAMPLE 22

In two separate experiments, propylene was passed into a reactor containing catalyst at 538° C., 1 atmosphere pressure, a helium/hydrocarbon ratio of 1.1 and a weight hourly space velocity of 3.10 hr$^{-1}$. The catalyst of the first experiment was hydrogen-form MCM-22 prepared as in Example 1 of U.S. Pat. No. 4,954,325 (hereinafter Example 24). The catalyst of the second experiment was the Example 18 product. After 20 minutes on stream, the product distribution, in weight percent, was determined to be as shown in Table 33. Significant propylene aromatization selectivity to benzene is observed for the Example 18 catalyst compared to MCM-22. The benzene yield over the Example 18 catalyst was 7.16 wt. %, compared to 2.64 wt. % for MCM 22.

TABLE 33
PROPYLENE AROMATIZATION

| Catalyst | MCM-22 | Example 6 |
|---|---|---|
| Product Dist., wt % | | |
| $C_1$ | 0.35 | 1.28 |
| $C_2=$ | 1.59 | 8.72 |
| $C_2$ | 12.82 | 0.00 |
| $C_3=$ (approx) | 0.00 | 41.87 |
| $C_3$ (approx) | 34.58 | 0.00 |
| Iso-$C_4$ | 9.28 | 2.73 |
| N−$C_4$ | 2.65 | 0.00 |
| Iso + 1 = $C_4=$ | 4.58 | 5.51 |
| C-$C_4=$ | 1.72 | 2.31 |
| T-$C_4=$ | 2.49 | 1.82 |
| N-$C_5$ | 0.24 | 0.10 |
| Cyclo-$C_5$ | 0.59 | 0.19 |
| Iso-$C_5$ | 2.27 | 0.93 |
| $C_5=$ | 2.25 | 2.94 |
| $C_6$ Par. | 1.04 | 0.52 |
| $C_6=$ | 0.18 | 0.22 |
| $C_7$ Par. + Ol. | 0.22 | 0.12 |
| $C_8$-$C_{12}$ Par. + Ol. | 0.00 | 0.00 |
| $C_{13}+$ Par. + Ol. | 0.00 | 0.00 |
| Benzene | 2.64 | 7.16 |
| Toluene | 9.08 | 8.10 |
| $C_8$ Ar. | 7.52 | 6.78 |
| $C_9$ Ar. | 3.01 | 3.87 |
| $C_{10}$-$C_{11}$ Ar. | 0.29 | 0.91 |
| $C_{12}+$ Ar. | 0.00 | 0.00 |
| Naphthalene | 0.38 | 0.77 |
| M-Naphthalenes | 0.26 | 3.16 |

EXAMPLE 23

Sodium aluminate comprising 40 wt. % $Al_2O_3$, 33 wt. % $Na_2O$, and 27 wt. % $H_2O$ was added to a solution containing NaOH and $H_2O$ in an autoclave. Ultrasil precipitated silica was then added with agitation, followed by aminocycloheptane (R) directing agent to form a reaction mixture.

This mixture had the following composition, in mole ratios:

| | |
|---|---|
| $SiO_2/Al_2O_3$ = | 33.34 |
| $OH^-/SiO_2$ = | 0.18 |
| $Na/SiO_2$ = | 0.18 |
| $R/SiO_2$ = | 0.35 |
| $H_2O/SiO_2$ = | 18.83 |

Figure 11:
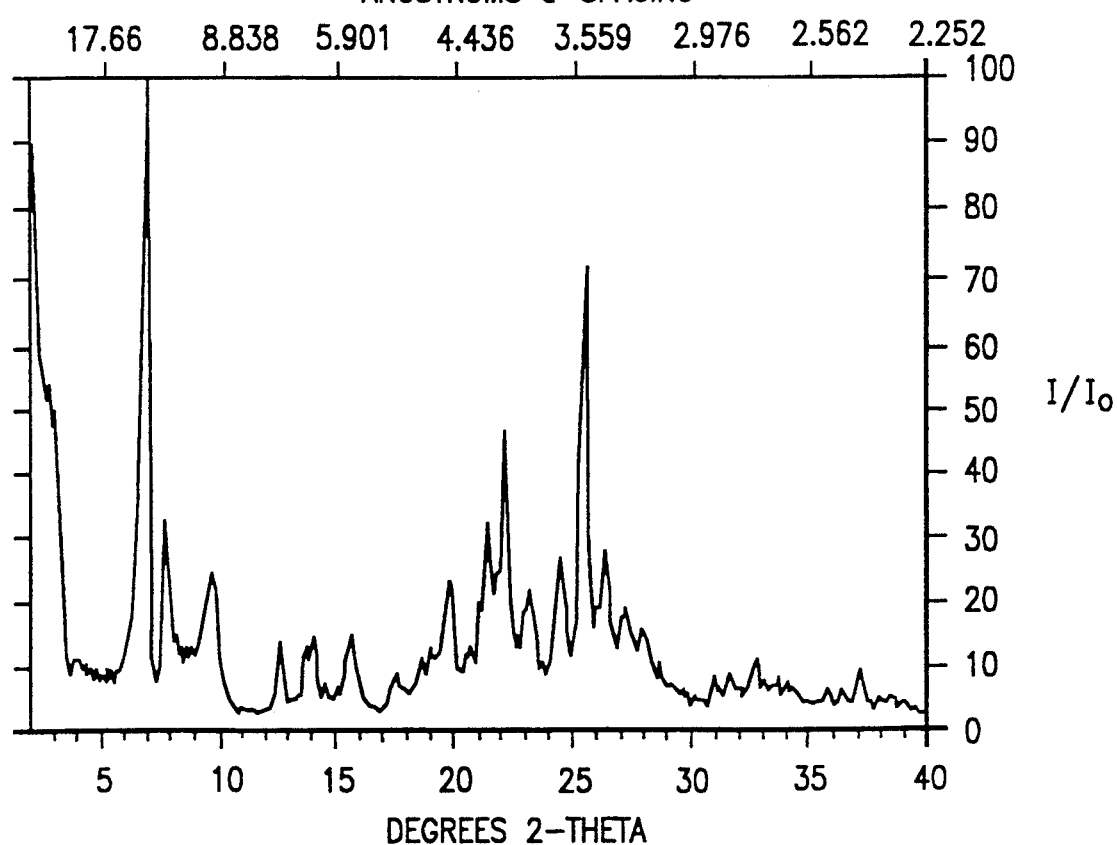
FIG. 11 is an X-ray diffraction pattern of the assynthesized crystalline material product of Example 23.

The mixture was crystallized at 143° C. for 192 hours with stirring. The product was identified as MCM-49 and had the X-ray pattern which appears in Table 34 and FIG. 11.

The chemical composition of the product was, in wt. %:

| | |
|---|---|
| N | 1.51 |
| Na | 0.83 |
| $Al_2O_3$ | 4.6 |
| $SiO_2$ | 74.2 |
| Ash | 79.2 |

The silica/alumina mole ratio of the product was 27.4.

The sorption capacities, after calcining at 538° C. for 9 hours were, in wt. %:

| | |
|---|---|
| Cyclohexane, 40 Torr | 7.5 |
| n-Hexane, 40 Torr | 14.0 |
| $H_2O$, 12 Torr | 13.5 |

TABLE 34

| Degrees 2-Theta | Interplanar d-spacing (A) | $I/I_o$ |
|---|---|---|
| 4.1 | 21.4 | 1 |
| 6.87 | 12.87 | 41 |
| 7.14 | 12.38 | 100 |
| 7.98 | 11.09 | 26 |
| 9.88 | 8.95 | 18 |
| 12.85 | 6.89 | 14 |
| 14.00 | 6.33 | 10 |
| 14.31 | 6.19 | 11 |
| 14.74 | 6.01 | 2 |
| 15.88 | 5.58 | 13 |
| 17.79 | 4.99 | 4 |
| 18.95 | 4.68 | 6 |
| 19.34 | 4.59 | 7 |
| 20.20 | 4.40 | 18 |
| 21.06 | 4.22 | 7 |
| 21.51 | 4.13 | 12 |
| 21.82 | 4.07 | 27 |
| 22.63 | 3.93 | 46 |
| 23.60 | 3.77 | 19 |
| 24.90 | 3.58 | 25 |
| 25.14 | 3.54 | 7 |
| 25.92 | 3.44 | 90 |
| 26.82 | 3.32 | 26 |
| 27.66 | 3.22 | 13 |
| 28.43 | 3.14 | 12 |
| 29.03 | 3.08 | 4 |
| 29.45 | 3.03 | 3 |
| 31.51 | 2.839 | 4 |
| 32.15 | 2.784 | 5 |
| 33.24 | 2.695 | 8 |
| 34.13 | 2.627 | 4 |
| 34.84 | 2.575 | 2 |
| 36.26 | 2.477 | 3 |
| 36.97 | 2.431 | 3 |
| 37.73 | 2.384 | 7 |

EXAMPLE 24

For comparison purposes, Example 1 of U.S. Pat. No. 4,954,325, incorporated herein by reference, was repeated. The as-synthesized crystalline material of the Example, referred to herein as MCM-22 precursor or the precursor form of MCM-22, was examined by X-ray diffraction analysis. Its X-ray diffraction pattern is presented in Table 35. The X-ray diffraction pattern of the calcined form of this material (538° C. for 20 hours) is shown in Table 36 below, and in FIG. 1 of U.S. Pat. No. 4,954,325.

TABLE 35

| Degrees 2-Theta | Interplanar d-spacing (A) | $I/I_o$ |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |

TABLE 35-continued

| Degrees 2-Theta | Interplanar d-spacing (A) | $I/I_o$ |
|---|---|---|
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

TABLE 36

| Degrees 2-Theta | Interplanar d-spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 19.08 | 4.65 | 2 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 25.01 | 3.56 | 20 |
| 26.00 | 3.43 | 100 |
| 26.96 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

The amount of catalyst used in the present process can be varied over relatively wide limits. In general, the amount of catalyst as measured by the weight hourly space velocity of the olefin can range from about 0.01 to about 10 $hr^{-1}$. The amount of catalyst selected for a particular reaction will be determined by several variables including the reactants involved as well as the nature of the catalyst and the operating conditions used.

EXAMPLES 25-33

Isoparaffin-Olefin Alkylation over Synthetic Crystalline Materials

Examples 25-33 show isoparaffin-olefin alkylation over different synthetic crystalline materials. These experiments evaluated the effects of altering reaction zone temperature and pressure, on the alkylation activity, selectivity, and longevity of various synthetic crystalline materials. While several materials appeared promising under start-of-run conditions, their alkylation performance generally deteriorated with increasing time on stream. For a crystalline material to be a viable candidate for commercialization, it must retain a useful level of catalytic activity over time, preferably to maximize time on stream between regenerations or catalyst replacements. The following examples surprisingly showed that controlling temperature and pressure to maintain the principal component of the feed in the supercritical state not only improves start-of-run performance, but also prolongs the useful life of the solid catalyst (i.e., the synthetic crystalline material).

Experimental Procedure

The following experiments were performed in a fixed-bed reactor. Typically, 5 grams of catalyst (30/60 mesh) was loaded into a fixed-bed reactor and the catalyst was heated overnight in a stream of nitrogen at the operating temperature and pressure. A pre-mixed hydrocarbon feed (obtained from Matheson and used as received) was introduced to initiate the run.

The hydrocarbon product, after depressurizing, was passed through a glass condenser. The condensed liquid and off-gas were analyzed separately by gas chromatography to determine conversion and selectivity.

Example 25-27 in Table 37 shows the effect of temperature on the activity and selectivity of MCM-36/Al$_2$O$_3$ catalyst. In each example the reactor pressure is 600 psig and is above the critical pressure of isobutane, the principal feed component. In example 25 and 26, where the reactor temperature is at or above the critical temperature of isobutane, the olefin conversion is maintained at >99 wt %. However, in example 27, where the reactor temperature is below the critical temperature of i-butane, the olefin conversion decreases significantly to 86.3%.

TABLE 37

Fixed-bed Alkylation with MCM-36/Al$_2$O$_3$
Comparison of Subcritical Versus Supercritical Temperature Conditions

| Example No. | 25 | 26 | 27 |
|---|---|---|---|
| Reaction Conditions: | | | |
| Feed I/O | 50 | 50 | 50 |
| R × R Pressure (psig) | 600 | 600 | 600 |
| $C_4^= WHSV (hr^{-1})$ | 0.05 | 0.05 | 0.05 |
| R × R Temp (°F.) | 300 | 275 | 250 |
| Time on Stream (days) | 2.7 | 3.2 | 3.7 |
| $C_4^=$ Conv. (wt %) | 99.4 | 99.0 | 86.3 |
| $C_5+$ Yield (gram/gram $C_4^=$ Conv.) | 2.0 | 1.9 | 1.6 |
| $C_5+$ Analysis: | | | |
| $C_5-C_7$ | 34 | 28 | 16 |
| Total $C_8$ | 50 | 53 | 62 |
| $C_9+$ | 17 | 19 | 22 |
| Total Unk. $C_8$ | 1.0 | 3.2 | 14 |
| TMP/DMH | 2.3 | 2.6 | 3.0 |
| TMP/(DMH + Unk. $C_8$) | 2.1 | 2.1 | 1.1 |

TABLE 38

Critical Constants of Various Hydrocarbons

| Hydrocarbon | Critical Constants Temperature (°F.) | Pressure (psia) |
|---|---|---|
| i-Butane | 275.0 | 529.1 |
| n-Butane | 305.6 | 550.7 |
| 1-Butene | 295.6 | 583.0 |
| cis-2-Butene | 324.3 | 600.0 |
| trans-2-Butene | 311.9 | 600.0 |
| i-Butylene | 292.5 | 579.8 |

Examples 28-33 in Table 39 show the effect of pressure on the activity and selectivity of MCM-22/Al$_2$O$_3$, MCM-49/Al₂O₃, and MCM-36/Al₂O₃ catalysts. In each example the reactor temperature is 300° F. and is above the critical temperature of isobutane, the principal feed component. With each catalyst high olefin conversion is obtained at 700 psig which is above the critical pressure of i-butane. However, with each catalyst the olefin conversion is significantly reduced when the reactor pressure is reduced to 500 psig which is below the critical pressure of isobutane.

TABLE 39

Alkylation with Zeolite/Al₂O₃ Catalysts
Comparison of Subcritical versus Supercritical Pressure Conditions

| Catalyst | MCM-22/Al₂O₃ Extrudate | | MCM-49/Al₂O₃ Extrudate | | MCM-36/Al₂O₃ Extrudate | |
|---|---|---|---|---|---|---|
| Example No. | 28 | 29 | 30 | 31 | 32 | 33 |
| Reaction Conditions: | | | | | | |
| Feed I/O | 50 | 50 | 50 | 50 | 50 | 50 |
| R × R Pressure (psig) | 500 | 700 | 500 | 700 | 500 | 700 |
| R × R Temperature (°F.) | 300 | 300 | 300 | 300 | 300 | 300 |
| Time on Stream (days) | 1.5 | 1.6 | 0.5 | 0.6 | 6 | 22 |
| $C_4=$ WHSV (hr$^{-1}$) | 0.05 | 0.05 | 0.05 | 0.05 | 0.05 | 0.05 |
| $C_4=$ Conv. (wt %) | 46.7 | 92.5 | 86.2 | 99.3 | 92.4 | 99.3 |
| $C_5+$ yield (gram/gram $C_4=$ Conv.) | 1.6 | 1.8 | 1.6 | 1.9 | 1.6 | 1.9 |
| $C_5+$ Analysis: | | | | | | |
| $C_5-C_7$ | 10 | 22 | 26 | 28 | 26 | 33 |
| Total $C_8$ | 73 | 63 | 60 | 58 | 56 | 53 |
| $C_9+$ | 17 | 15 | 14 | 15 | 18 | 14 |
| Unknown $C_8$ | 19 | 5.0 | 5.2 | 2.0 | 4.4 | 1.1 |
| TMP/DMH | 2.3 | 2.9 | 3.2 | 3.0 | 2.1 | 2.3 |
| TMP/(DMH + Unk. $C_8$) | 1.1 | 2.2 | 2.3 | 2.6 | 1.6 | 2.2 |

Figure 12:
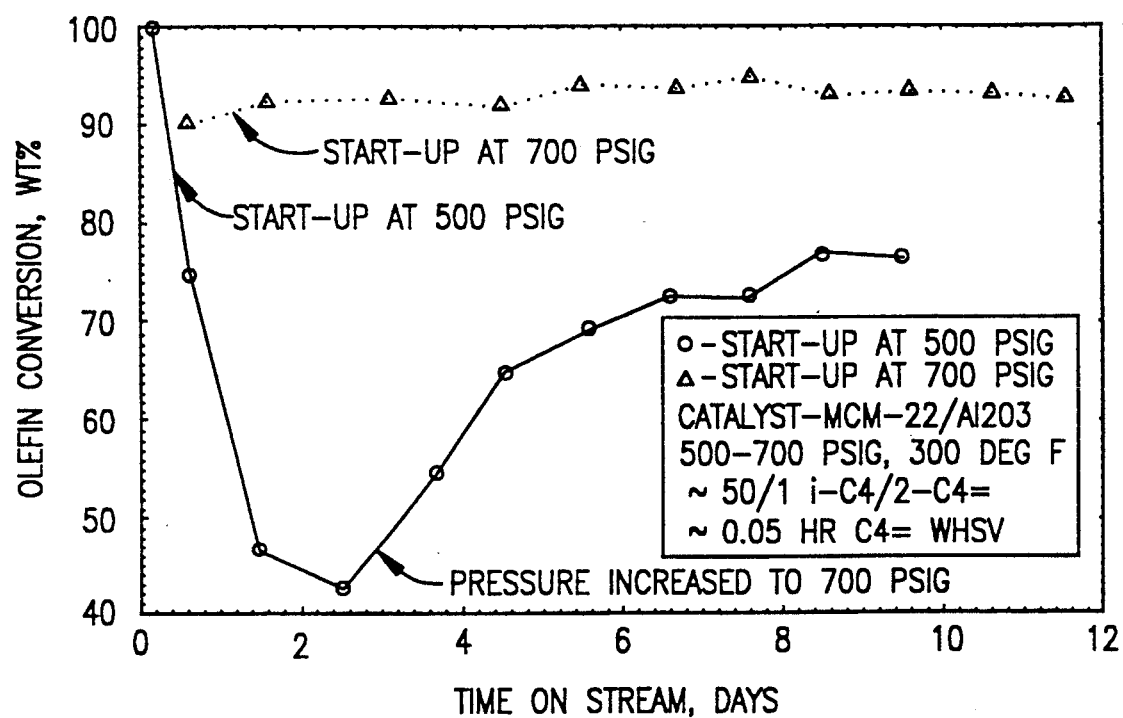
FIG. 12 shows weight percent olefin conversion as a function of days on stream for isobutane/2-butenes alkylation in the presence of an MCM-22/Al$_2$O$_3$ extrudate. Triangular datapoints show operation under supercritical conditions (700 psig and 300° F.) while the circular datapoints show operation started under less severe conditions (500 psig and 300° F.) for isobutane/2-butane alkylation.

Examples 25–33 show the improvement in isoparaffin-olefin alkylation activity resulting from maintaining reaction conditions above the critical values for the principal component of the feed. The alkylation process of the invention is preferably started and maintained under supercritical condition, as shown in FIG. 12. FIG. 12 shows the improvement in catalyst stability when the startup is carried out at 700 psig and 300° F. The circular datapoints in FIG. 12 represent data from a run where the startup is carried out at 500 psig and 300° F. Starting at 100%, the olefin conversion decreased rapidly to less than about 50% within 2.5 days on stream. Increasing the pressure to 700 psig improved the conversion but the conversion remained below 80%. On the other hand, starting and maintaining the run under supercritical conditions provided olefin conversion of greater than about 95% for more than 6 days on stream, as shown by the triangular datapoints in FIG. 12.

Changes and modifications in the specifically described embodiments can be carried out without departing from the scope of the invention which is intended to be limited only by the scope of the appended claims.

What is claimed is:

1. A method for increasing olefin conversion in the catalytic alkylation of an olefin with an isoparaffin comprising contacting an olefin-containing feed with an isoparaffin-containing feed with a crystalline microporous material selected from the group consisting of MCM-22, MCM-36, and MCM-49 as defined herein under alkylation conversion conditions of temperature at least equal to the critical temperature of the principal isoparaffin component of the feed and pressure at least equal to the critical pressure of the principal isoparaffin component of the feed.

2. The process of claim 1 wherein said crystalline microporous material has the structure of at least one selected from the group consisting of MCM-36 and MCM-49, as defined herein.

3. A method for increasing the useful life of a crystalline microporous alkylation catalyst in a process for alkylating an olefin with an isoparaffin comprising contacting an olefin-containing feed with an isoparaffin-containing feed with said crystalline microporous material selected from the group consisting of MCM-22, MCM-36, and MCM-49 as described herein, under alkylation conversion conditions of temperature at least equal to the critical temperature of the principal isoparaffin component of the feed and pressure at least equal to the critical pressure of the principal isoparaffin component of the feed, without contacting said isoparaffin-containing feed with said crystalline microporous material at temperature below the critical temperature of the principal isoparaffin component of the feed or at pressure below the critical pressure of the principal isoparaffin component of the feed.

* * * * *